United States Patent
Kuang et al.

(10) Patent No.: US 11,952,397 B2
(45) Date of Patent: Apr. 9, 2024

(54) CRYSTALLINE FORMS OF A NEUROACTIVE STEROID

(71) Applicant: Sage Therapeutics, Inc., Cambridge, MA (US)

(72) Inventors: Shanming Kuang, Plainsboro, NJ (US); Tianrui Li, Cambridge, NJ (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 18/363,942

(22) Filed: Aug. 2, 2023

(65) Prior Publication Data

US 2023/0374061 A1 Nov. 23, 2023

Related U.S. Application Data

(63) Continuation of application No. PCT/US2022/038459, filed on Jul. 27, 2022.

(60) Provisional application No. 63/226,374, filed on Jul. 28, 2021.

(51) Int. Cl.
*C07J 43/00* (2006.01)

(52) U.S. Cl.
CPC .................. *C07J 43/003* (2013.01)

(58) Field of Classification Search
CPC ........................................ C07J 43/003
See application file for complete search history.

(56) References Cited

U.S. PATENT DOCUMENTS

| | | |
|---|---|---|
| 7,729,773 B2 | 6/2010 | Sloan |
| 11,236,121 B2 | 2/2022 | Watson et al. |
| 2004/0133119 A1 | 7/2004 | Osorio et al. |
| 2018/0179247 A1 | 6/2018 | Botella et al. |
| 2020/0165291 A1 | 5/2020 | Martinez Botella et al. |
| 2021/0061849 A1 | 3/2021 | Botella et al. |
| 2021/0061850 A1 | 3/2021 | Martinez Botella et al. |
| 2022/0169674 A1 | 6/2022 | Watson et al. |

FOREIGN PATENT DOCUMENTS

| | | |
|---|---|---|
| WO | 2013056181 A1 | 4/2013 |
| WO | 2017156103 A1 | 9/2017 |
| WO | 2022221195 A1 | 10/2022 |

OTHER PUBLICATIONS

Anonymous: "History of Changes for Study: NCT04305275; A Study to Evaluate the Efficacy, Safety and Tolerability of Sage-324 in Participants with Essential Tremor", ClinicalTrials.gov archive, Mar. 2, 2021 (Mar. 3, 2021), pp. 1-6, XP055940666, Retrieved from the Internet: URL: https://clinicaltrials.gov/ct2/history/NCT04305275?V_9=View#StudyPageTop [retrieved on Jul. 11, 2022] sections "Study Design" and "Arms and Interventions" on p. 2 and 3.

Bankole K : "LBA10: SAGE-324/BIIB124, an oral neuroactive steroid (NAS) GABA-A receptor positive allosteric modulator (PAM), in patients with essential tremor: results from the phase 2 Kinetic trial", MDS Virtual Congress 2021 Late-Breaking Abstracts, Sep. 17, 2021 (Sep. 17, 2021) pp. 1-13, XP055940686, Retrieved from the Internet: URL: https://www.mdscongress.org/MDS-Files1/MDSVirtualCongress2021Late-BreakingAbstractPublication.pdf> Abstract LBA10.

Caira, M.R., "Crystalline Polymorphism of Organic Compounds", Topics in Current Chemistry, vol. 198, 1998, pp. 163-208.

Colquhoun H: "Abstract 79: An Open-Label, Phase 1b Study of the Neuroactive Steroid GABAA Receptor Positive Allosteric Modulator SAGE-324 in Essential Tremor", MDS Virtual Congress 2020, Sep. 12, 2020 (Sep. 12, 2020), pp. 1-2, XP055940712, Retrieved from the Internet: URL: https://www.mdsabstracts.org/abstract/an-open-label-phase-1b-study-of-the-neuroactive-steroid-gabaa-receptor-positive-allosteric-modulator-sage-324-in-essential-tremor/> Abstract 79.

Int. Search Report for PCT/US2022/024264.
Int. Search Report for PCT/US2022/038459.
Singhal, D., et al., "Drug Polymorphism and dosage form design: a practical perspective", Advanced Drug Delivery Reviews, 2004, vol. 56, pp. 335-347.
Written Opinion for PCT/US2022/038459.
Written Opinion for PCT/US2022/024264.
U.S. Appl. No. 15/649,583, filed Jul. 13,2017, U.S. Pat. No. 10,322,139, Issued.
U.S. Appl. No. 16/396,065, filed Apr. 26, 2019, U.S. Pat. No. 11,426,417, Issued.
U.S. Appl. No. 17/869,145, filed Jul. 20, 2022, Published.
U.S. Appl. No. 17/592,244, filed Feb. 3, 2022, Published.

(Continued)

*Primary Examiner* — Samantha L Shterengarts
*Assistant Examiner* — Karen Cheng
(74) *Attorney, Agent, or Firm* — Honigman LLP; Andrew N. Weber; Jonathan P. O'Brien

(57) ABSTRACT

This invention relates to crystalline forms of anhydrous Compound (1) and pharmaceutical compositions thereof. Also disclosed herein are methods of making crystalline solid forms of Compound (1), and methods of using the crystalline forms of Compound (1) and pharmaceutical compositions thereof for modulating GABA activity (e.g., positive allosteric modulation of GABA activity) and treating CNS-related disorders.

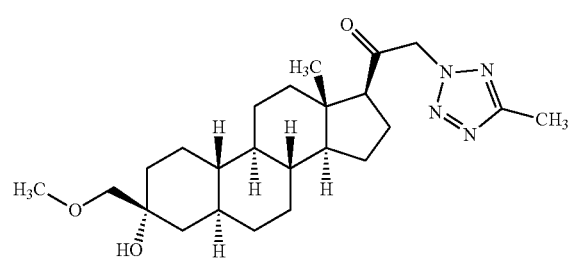

(1)

7 Claims, 12 Drawing Sheets

(56) References Cited

OTHER PUBLICATIONS

U.S. Appl. No. 15/681,983, filed Aug. 21, 2017, U.S. Pat. No. 10,435,431, Issued.
U.S. Appl. No. 17/077,025, filed Oct. 22, 2020, Abandoned.
U.S. Appl. No. 15/698,151, filed Sep. 7, 2017, U.S. Pat. No. 10,323,059, Issued.
U.S. Appl. No. 16/393,396, filed Apr. 24, 2019, U.S. Pat. No. 11,046,728, Issued.
U.S. Appl. No. 15/143,312, field Apr. 29, 2016, U.S. Pat. No. 10,377,790, Issued.
U.S. Appl. No. 16/440,527, filed Jun. 13, 2019, U.S. Pat. No. 11,261,211, Issued.
U.S. Appl. No. 14/785,192, filed Oct. 16, 2015, U.S. Pat. No. 9,365,611, Issued.
U.S. Appl. No. 15/273,125, filed Sep. 22, 2016, U.S. Pat. No. 10,023,606, Issued.
U.S. Appl. No. 16/007,556, filed Jun. 13, 2018, U.S. Pat. No. 10,822,370, Issued.
U.S. Appl. No. 17/067,093, field Oct. 9, 2020, Published.
U.S. Appl. No. 14/785,171, filed Oct. 16, 2015, U.S. Pat. No. 9,512,165, Issued.
U.S. Appl. No. 15/297,845, filed Oct. 19, 2016, U.S. Pat. No. 10,172,871, Issued.
U.S. Appl. No. 16/020,641, filed Jun. 27, 2018, U.S. Pat. No. 10,342,810, Issued.
U.S. Appl. No. 16/428,386, filed May 31, 2019, U.S. Pat. No. 11,241,446, Issued.
U.S. Appl. No. 17/560,732, filed Dec. 23, 2021, Published.
U.S. Appl. No. 15/639,702, filed Jun. 30, 2017, U.S. Pat. No. 10,391,106, Issued.
U.S. Appl. No. 16/507,214, filed Jul. 10, 2019, U.S. Pat. No. 11,344,563, Issued.
U.S. Appl. No. 14/785,175, filed Oct. 16, 2015, U.S. Pat. No. 9,725,481, Issued.
U.S. Appl. No. 16/843,822, filed Apr. 8, 2020, U.S. Pat. No. 11,498,940, Issued.
U.S. Appl. No. 14/132,386, filed Dec. 18, 2013, U.S. Pat. No. 9,630,986, Issued.
U.S. Appl. No. 15/459,492, filed Mar. 15, 2017, U.S. Pat. No. 10,342,809, Issued.
U.S. Appl. No. 16/419,255, filed May 22, 2019, Abandoned.
U.S. Appl. No. 14/652,717, filed Jun. 16, 2015, U.S. Pat. No. 9,676,812, Issued.
U.S. Appl. No. 17/304,433, filed Jun. 21, 2021, Published.
U.S. Appl. No. 17/094,783, filed Nov. 10, 2020, Abandoned.
U.S. Appl. No. 15/314,565, filed Nov. 29, 2016, Published.
U.S. Appl. No. 15/531,313, filed May 26, 2017, U.S. Pat. No. 10,774,108, Issued.
U.S. Appl. No. 16/800,053, filed Feb. 25, 2020, Abandoned.
U.S. Appl. No. 15/319,503, filed Dec. 16, 2016, U.S. Pat. No. 10,246,482, Issued.
U.S. Appl. No. 16/269,779, filed Feb. 7, 2019, U.S. Pat. No. 10,745,436, Issued.
U.S. Appl. No. 16/924,814, filed Jul. 9, 2020, U.S. Pat. No. 11,149,057, Issued.
U.S. Appl. No. 17/472,744, filed Sep. 13, 2021, Allowed.
U.S. Appl. No. 16/786,160, filed Feb. 10, 2020, Published.
U.S. Appl. No. 16/748,117, filed Jan. 21, 2020, U.S. Pat. No. 11,530,237, Issued.
U.S. Appl. No. 17/694,896, filed Mar. 15, 2022, Abandoned.
U.S. Appl. No. 17/695,033, filed Mar. 15, 2022, U.S. Pat. No. 11,542,297, Issued.
U.S. Appl. No. 15/519,480, filed Apr. 14, 2017, U.S. Pat. No. 10,577,390, Issued.
U.S. Appl. No. 16/365,123, filed Mar. 26, 2019, U.S. Pat. No. 10,870,677, Issued.
U.S. Appl. No. 17/112,125, filed Dec. 4, 2020, Abandoned.
U.S. Appl. No. 15/660,114, filed Jul. 26, 2017, U.S. Pat. No. 10,426,837, Issued.
U.S. Appl. No. 16/545,727, filed Aug. 20, 2019, U.S. Pat. No. 11,147,877, Issued.
U.S. Appl. No. 16/399,529, filed Apr. 30, 2019, U.S. Pat. No. 11,124,538, Issued.
U.S. Appl. No. 17/144,302, filed Jan. 8, 2021, Abandoned.
U.S. Appl. No. 15/552,201, filed Aug. 18, 2017, U.S. Pat. No. 10,329,320, Issued.
U.S. Appl. No. 17/134,929, filed Dec. 28, 2020, Published.
U.S. Appl. No. 16/423,976, filed May 28, 2019, Abandoned.
U.S. Appl. No. 15/649,460, filed Jul. 13, 2017, U.S. Pat. No. 10,426,786, Issued.
U.S. Appl. No. 16/544,480, filed Aug. 19, 2019, U.S. Pat. No. 11,510,929, Issued.
U.S. Appl. No. 17/064,517, filed Oct. 6, 2020, Published.
U.S. Appl. No. 15/917,245, filed Mar. 9, 2018, U.S. Pat. No. 10,251,894, Issued.
U.S. Appl. No. 17/401,787, filed Aug. 13, 2021, Published.
U.S. Appl. No. 16/718,430, filed Dec. 18, 2019, U.S. Pat. No. 10,940,156, Issued.
U.S. Appl. No. 17/195,129, filed Mar. 8, 2021, U.S. Pat. No. 11,554,125, Issued.
U.S. Appl. No. 17/242,913, filed Apr. 28, 2021, Published.
U.S. Appl. No. 17/837,426, filed Jun. 10, 2022, Published.
U.S. Appl. No. 16/316,853, filed Jan. 10, 2019, U.S. Pat. No. 11,396,525, Issued.
U.S. Appl. No. 17/396,464, filed Aug. 6, 2021, Published.
U.S. Appl. No. 16/326,977, filed Feb. 21, 2019, U.S. Pat. No. 11,236,121, Issued.
U.S. Appl. No. 16/955,736, filed Jun. 18, 2020, Published.
U.S. Appl. No. 16/644,680, filed Mar. 5, 2020, Abandoned.
U.S. Appl. No. 17/251,475, filed Dec. 11, 2020, Published.
U.S. Appl. No. 16/647,203, filed Mar. 13, 2020, Abandoned.
U.S. Appl. No. 16/645,975, filed Mar. 10, 2020, Published.
U.S. Appl. No. 17/545,290, filed Dec. 8, 2021, U.S. Pat. No. 11,667,668, Issued.
U.S. Appl. No. 16/961,097, filed Jul. 9, 2020, U.S. Pat. No. 11,718,642, Issued.
U.S. Appl. No. 16/955,714, filed Jun. 18, 2020, Published.
U.S. Appl. No. 17/286,524, filed Apr. 19, 2021, Published.
U.S. Appl. No. 17/284,206, filed Apr. 9, 2021, U.S. Pat. No. 11,634,453, Issued.
U.S. Appl. No. 17/311,056, filed Jun. 24, 2021, Published.
U.S. Appl. No. 17/416,367, filed Jun. 18, 2021, Published.
U.S. Appl. No. 63/322,725, filed Mar. 23, 2022, Expired.
U.S. Appl. No. 16/887,887, filed May 29, 2020, U.S. Pat. No. 11,643,434, Issued.
U.S. Appl. No. 17/579,541, filed Jan. 19, 2022, Published.
U.S. Appl. No. 17/620,226, filed Dec. 17, 2021, Published.
U.S. Appl. No. 17/620,275, filed Dec. 17, 2021, Pending.
U.S. Appl. No. 17/782,362, filed Jun. 3, 2022, Published.
U.S. Appl. No. 17/843,031, filed Jun. 17, 2022, Published.
U.S. Appl. No. 17/620,303, filed Dec. 17, 2021, Published.
U.S. Appl. No. 63/289,296, filed Dec. 14, 2021, Expired.
U.S. Appl. No. 63/284,592, filed Nov. 30, 2021, Expired.
U.S. Appl. No. 63/181,743, filed Apr. 29, 2021, Expired.
U.S. Appl. No. 63/197,025, filed Jun. 4, 2021, Expired.
U.S. Appl. No. 63/289,506, filed Dec. 14, 2021, Expired.
U.S. Appl. No. 63/181,807, filed Apr. 29, 2021, Expired.
U.S. Appl. No. 63/210,810, filed Jun. 15, 2021, Expired.
U.S. Appl. No. 63/239,096, filed Aug. 31, 2021, Expired.
U.S. Appl. No. 63/285,812, filed Dec. 3, 2021, Expired.
U.S. Appl. No. 63/289,520, filed Dec. 14, 2021, Expired.
U.S. Appl. No. 63/298,601, filed Jan. 11, 2022, Expired.
U.S. Appl. No. 63/392,579, filed Jul. 27, 2022, Expired.
U.S. Appl. No. 63/310,581, filed Feb. 16, 2022, Expired.
U.S. Appl. No. 63/337,828, filed May 3, 2022, Expired.
U.S. Appl. No. 63/310,583, filed Feb. 16, 2022, Expired.
U.S. Appl. No. 63/310,585, filed Feb. 16, 2022, Expired.
U.S. Appl. No. 63/315,006, filed Feb. 28, 2022, Expired.
U.S. Appl. No. 63/315,015, filed Feb. 28, 2022, Expired.
U.S. Appl. No. 63/315,026, filed Feb. 28, 2022, Expired.
U.S. Appl. No. 63/315,038, filed Feb. 28, 2022, Expired.
U.S. Appl. No. 17/969,105, filed Oct. 19, 2022, Expired.

(56) References Cited

OTHER PUBLICATIONS

U.S. Appl. No. 17/993,020, filed Nov. 23, 2022, Pending.
U.S. Appl. No. 18/087,870, filed Dec. 23, 2022, Published.
U.S. Appl. No. 18/169,964, filed Feb. 16, 2023, Published.
U.S. Appl. No. 18/162,025, filed Jan. 31, 2023, Pending.
U.S. Appl. No. 18/107,965, filed Feb. 9, 2023, Published.
U.S. Appl. No. 18/349,218, filed Jul. 10, 2023, Pending.
U.S. Appl. No. 63/442,059, filed Jan. 30, 2023, Pending.
U.S. Appl. No. 63/442,056, filed Jan. 30, 2023, Pending.
U.S. Appl. No. 63/442,005, filed Jan. 30, 2023, Pending.
U.S. Appl. No. 63/442,027, filed Jan. 30, 2023, Pending.
U.S. Appl. No. 18/334,124, filed Jun. 13, 2023, Pending.
U.S. Appl. No. 18/334,189, filed Jun. 13, 2023, Pending.
U.S. Appl. No. 18/334,209, filed Jun. 13, 2023, Pending.

CRYSTALLINE FORMS OF A NEUROACTIVE STEROID

CROSS REFERENCE TO RELATED APPLICATION

This U.S. application is a continuation of PCT application no. PCT/US2022/038459, filed Jul. 27, 2022, which claims the benefit of U.S. provisional application no. 63/226,374, filed on Jul. 28, 2021, the entire contents of which is hereby incorporated herein by reference in its entirety.

FIELD OF THE INVENTION

The present invention relates to solid (e.g., crystalline) forms of a neuroactive steroid that are useful for modulating (e.g., selectively modulating) the activity of certain GABA receptors and treating or reducing the severity of CNS-related disorders in patients, and prophylactically preventing or reducing the incidence of symptoms of CNS-related disorders in patients.

BACKGROUND

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the γ-aminobutyric acid receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

New and improved crystalline forms of neuroactive steroids are needed that act as modulating agents for brain excitability, as well as agents for the prevention and treatment of CNS-related diseases. Crystalline forms of such a neuroactive steroid described herein are directed toward this end.

SUMMARY OF THE INVENTION

The present invention provides a crystalline form of Compound (1), wherein Compound (1) is represented by the following structural formula:

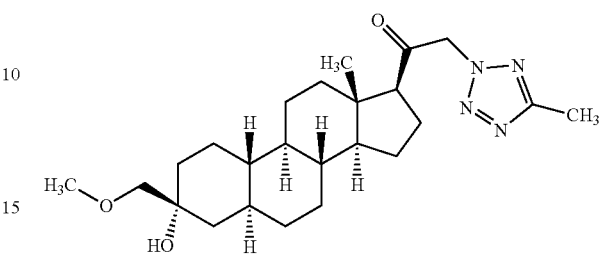

Compound (1), and wherein the crystalline form is crystalline anhydrous Compound (1).

In some embodiments, the crystalline form is characterized by one or more peaks corresponding to 2-theta values measured in degrees of 15.4±0.3, 15.6±0.3, 18.1±0.3, 18.8±0.3, and 22.6±0.3 in an X-ray powder diffraction pattern. In other embodiments, the crystalline form is further characterized by one or more peaks corresponding to 2-theta values measured in degrees of 9.4±0.3, 11.9±0.3, 22.2±0.3, and 23.4±0.3 in an X-ray powder diffraction pattern.

In some embodiments, the crystalline form is characterized by one or more peaks corresponding to 2-theta values measured in degrees of 15.4±0.2, 15.6±0.2, 18.1±0.2, 18.8±0.2, and 22.6±0.2 in an X-ray powder diffraction pattern. In other embodiments, the crystalline form is further characterized by one or more peaks corresponding to 2-theta values measured in degrees of 9.4±0.2, 11.9±0.2, 22.2±0.2, and 23.4±0.2 in an X-ray powder diffraction pattern.

In some embodiments, the crystalline form has an endotherm at a $T_{onset}$ from about 146° C. to about 157° C. when heated at a rate of 10° C./min starting at a temperature of about 30° C.

In some embodiments, the crystalline form is characterized by one or more peaks corresponding to 200.0±0.3 ppm, 164.3±0.3 ppm, 81.3±0.3 ppm, 70.5±0.3 ppm, and 62.2±0.3 ppm in a $^{13}C$ SSNMR spectrum. In some embodiments, the crystalline form is further characterized by one or more peaks corresponding to 60.9±0.3 ppm, 60.0±0.3 ppm, 56.7±0.3 ppm, 47.8±0.3 ppm, and 45.9±0.3 ppm in a $^{13}C$ SSNMR spectrum. In other embodiments, the crystalline form is further characterized by one or more peaks corresponding to 42.6±0.3 ppm, 39.3±0.3 ppm, 38.3±0.3 ppm, 35.5±0.3 ppm, 25.8±0.3 ppm, and 22.9±0.3 ppm in a $^{13}C$ SSNMR spectrum.

In some embodiments, the crystalline form is characterized by one or more peaks corresponding to 2-theta values measured in degrees of 8.9±0.3, 14.6±0.3, 16.4±0.3, 18.0±0.3, and 20.0±0.3 in an X-ray powder diffraction pattern. In some embodiments, the crystalline form is further characterized by one or more peaks corresponding to 2-theta values measured in degrees of 11.6±0.3, 15.0±0.3, 17.4±0.3, 21.2±0.3, and 29.0±0.3 in an X-ray powder diffraction pattern. In other embodiments, the crystalline form is further characterized by one or more peaks corresponding to 2-theta values measured in degrees of 9.6±0.3, 12.9±0.3, and 29.6±0.3 in an X-ray powder diffraction pattern.

In some embodiments, the crystalline form is characterized by one or more peaks corresponding to 2-theta values measured in degrees of 8.9±0.2, 14.6±0.2, 16.4±0.2, 18.0±0.2, and 20.0±0.2 in an X-ray powder diffraction pattern. In some embodiments, the crystalline form is further characterized by one or more peaks corresponding to 2-theta values measured in degrees of 11.6±0.2, 15.0±0.2, 17.4±0.2, 21.2±0.2, and 29.0±0.2 in an X-ray powder diffraction pattern. In other embodiments, the crystalline form is further characterized by one or more peaks corresponding to 2-theta values measured in degrees of 9.6±0.2, 12.9±0.2, and 29.6±0.2 in an X-ray powder diffraction pattern.

In some embodiments, the crystalline form has an endotherm at a $T_{onset}$ from about 160° C. to about 166° C. when heated at a rate of 10° C./min starting at a temperature of about 30° C. In other embodiments, the crystalline form (or Compound (1)) degrades at a temperature of about 200° C. or greater.

In some embodiments, the crystalline form is further characterized by one or more peaks corresponding to 200.2±0.3 ppm, 199.1±0.3 ppm, 162.8±0.3 ppm, 82.9±0.3 ppm, 82.1±0.3 ppm, and 12.6±0.3 ppm in a $^{13}C$ SSNMR spectrum. In some embodiments, the crystalline form is further characterized by one or more peaks corresponding to 70.4±0.3 ppm, 63.6±0.3 ppm, 49.7±0.3 ppm, 35.5±0.3 ppm, and 15.5±0.3 ppm in a $^{13}C$ SSNMR spectrum. In other embodiments, the crystalline form is further characterized by one or more peaks corresponding to 62.9±0.3 ppm, 61.4±0.3 ppm, 60.6±0.3 ppm, 45.4±0.3 ppm, and 37.9±0.3 ppm in a $^{13}C$ SSNMR spectrum.

In some embodiments, the crystalline form of Compound (1) is substantially pure. For instance, the crystalline form is substantially free of impurities (e.g., comprises fewer than about 30 wt % of impurities, fewer than about 25 wt % of impurities, fewer than about 10 wt % of impurities, fewer than about 5 wt % of impurities, fewer than about 1 wt % of impurities, fewer than about 0.5 wt % of impurities, fewer than about 0.1 wt % of impurities, or fewer than about 0.05 wt % of impurities).

Another aspect of the present invention provides a pharmaceutical composition comprising a crystalline form described herein, and a pharmaceutically acceptable excipient.

Another aspect of the present invention provides a method of modulating a $GABA_A$ receptor in a subject in need thereof, comprising administering to the subject a therapeutically effective amount of a crystalline form described herein or a pharmaceutical composition described herein.

Another aspect of the present invention provides a method of modulating a $GABA_A$ receptor mediated CNS-related disorder in a subject in need thereof, comprising administering to the subject a therapeutically effective amount of a crystalline form described herein or a pharmaceutical composition described herein.

Another aspect of the present invention provides a method of treating a CNS-related disorder in a subject in need thereof, comprising administering to the subject a therapeutically effective amount of a crystalline form described herein or a pharmaceutical composition described herein.

In some implementations, the CNS-related disorder is a sleep disorder, a mood disorder, a schizophrenia spectrum disorder, a convulsive disorder, a disorder of memory and/or cognition, a movement disorder, a personality disorder, an autism spectrum disorder, pain, traumatic brain injury, a vascular disease, a substance abuse disorder and/or withdrawal syndrome, tinnitus, or status epilepticus. For example, the CNS-related disorder is a mood disorder. In other examples, the mood disorder is depression. For instance, the depression is postpartum depression. In other instances, the depression is a major depressive disorder. For example, the major depressive disorder is a moderate major depressive disorder. And, in other examples, the major depressive disorder is a severe major depressive disorder.

In some implementations, the CNS-related disorder is tremor (e.g., essential tremor).

In some implementations, the CNS-related disorder is seizure.

In some implementations, the CNS-related disorder is epilepsy.

In some implementations, the CNS-related disorder is status epilepticus. For example, the status epilepticus is convulsive status epilepticus or non-convulsive status epilepticus. In some instances, the status epilepticus is convulsive status epilepticus selected from early status epilepticus, established status epilepticus, refractor status epilepticus, and super-refractory status epilepticus. In other instances, the status epilepticus is non-convulsive status epilepticus selected from generalized status epilepticus and partial complex status epilepticus.

Another aspect of the present invention provides a method for inducing sedation and/or anesthesia in a subject in need thereof, comprising administering to the subject an effective amount of a crystalline form described herein or a pharmaceutical composition described herein.

DESCRIPTION OF THE DRAWINGS

The following figures are presented by way of example and are not intended to limit the scope of the claimed invention.

DETAILED DESCRIPTION

Figure 1:
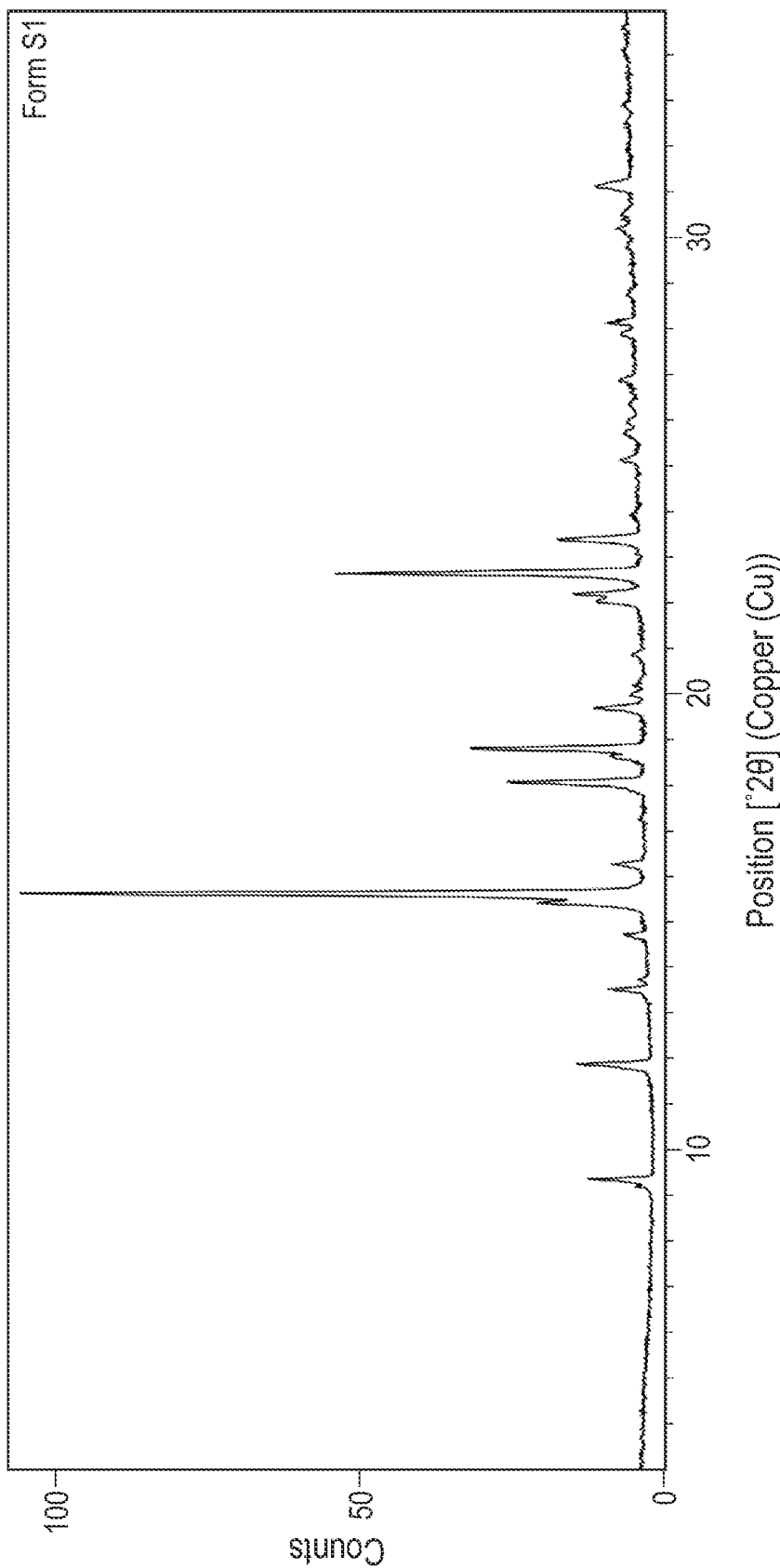
FIG. 1 depicts an exemplary XRPD pattern of Form S1 of Compound (1).

The present invention generally relates to crystalline forms (e.g., anhydrous crystalline forms) of Compound (1), pharmaceutically acceptable formulations thereof, methods of preparing such crystalline forms of Compound (1), and uses of such crystalline forms for modulating GABA receptor activity (e.g., positive allosteric modulation) and/or treating CNS-related disorders.

I. Definitions

As used herein, "Compound (1)" refers to the compound having the structure (or structural formula):

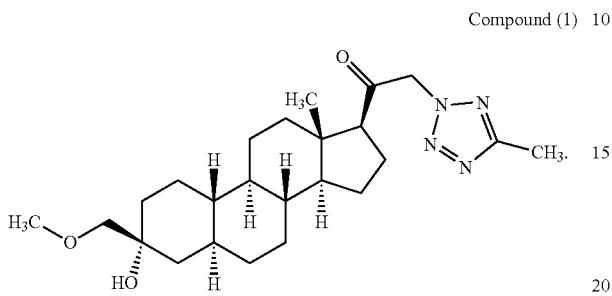

Compound (1)

As used herein, "XRPD" refers to X-ray powder diffraction.

As used herein, the term "VT-XRPD" refers to variable temperature XRPD.

As used herein, the terms "XRPD pattern" and "X-ray powder diffraction pattern" are used interchangeably and refer to a plot of intensity of X-rays scattered at different angles by a sample.

As used herein, "IPA" refers to isopropyl alcohol.

As used herein, "TGA" refers to thermogravimetric analysis.

As used herein, "DSC" refers to differential scanning calorimetry.

As used herein, "NMR" refers to nuclear magnetic resonance.

As used herein, "DVS" refers to dynamic vapor sorption.

As used herein, "DCM" refers to dichloromethane.

As used herein, "EtOAc" refers to ethyl acetate.

As used herein, "MeOH" refers to methanol.

As used herein, "MTBE" refers to methyl tert-butyl ether.

As used herein, "RH" refers to relative humidity.

As used herein, "RT" refers to room temperature.

As used herein, "HPLC" refers to high pressure liquid chromatography.

As used herein, "crystalline" refers to a solid having a highly regular chemical structure, i.e., having long range structural order in the crystal lattice. The molecules are arranged in a regular, periodic manner in the 3-dimensional space of the lattice. For the purposes of this application, the terms "crystalline form", "single crystalline form", "crystalline solid form", and "solid form" are synonymous and used interchangeably; the terms distinguish between crystals that have different properties (e.g., different XRPD diffraction patterns, different $^{13}$C SSNMR spectra, different DSC scan results, and/or different TGA scan results).

The term "substantially crystalline" refers to forms that may be at least a particular weight percent crystalline. Particular weight percentages are 70%, 75%, 80%, 85%, 87%, 88%, 89%, 90%, 91%, 92%, 93%, 94%, 95%, 96%, 97%, 98%, 99%, 99.5%, 99.9%, or any percentage between 70% and 100%. In certain embodiments, the particular weight percent of crystallinity is at least 90%. In certain other embodiments, the particular weight percent of crystallinity is at least 95%. In some embodiments, Compound (1) can be a substantially crystalline sample of any of the crystalline solid forms described herein (e.g., Forms S1 and S4).

The term "substantially pure" relates to the composition of a specific crystalline solid form of Compound (1) (e.g., Form S2 or Form S4) that is substantially free of any impurity and/or any other crystalline or solid form of Compound (1). In some examples, a substantially pure crystalline (or solid) form of Compound (1) (e.g., Form S1 or Form S4) or sample thereof is at least 90 wt %, at least 92 wt %, at least 94 wt %, at least 95 wt %, at least 96 wt %, at least 97 wt %, at least 98 wt %, at least 99 wt %, or at least at least 99.5 wt % pure. In some embodiments, Compound (1) can be a substantially pure sample of any of the crystalline solid forms described herein. (e.g., Forms S1 and S4). In some embodiments, Compound (1) can be substantially pure Form S1. In some embodiments, Compound (1) can be substantially pure Form S4.

As used herein, the term "anhydrous" or "anhydrate", when referring to a crystalline form of Compound (1), means that no solvent molecules, including those of water, form a portion of the unit cell of the crystalline form. A sample of an anhydrous crystalline form may nonetheless contain solvent molecules that do not form part of the unit cell of the anhydrous crystalline form, e.g., residual solvents left behind from the production of the crystalline form. In a preferred embodiment, a solvent can make up 0.5% by weight of the total composition of a sample of an anhydrous form. In a more preferred embodiment, a solvent can make up 0.2% by weight of the total composition of a sample of an anhydrous form. In some embodiments, a sample of an anhydrous crystalline form of Compound (1) contains no (or a very low level of) solvent molecules, e.g., no detectable amount of solvent.

As used herein, the term "solvate", when referring to a crystalline form of Compound (1), means that solvent molecules, e.g., organic solvents and/or water, form a portion of the unit cell of the crystalline form. Solvates that contain water as the solvent are also referred to herein as "hydrates".

As used herein, the term "isomorphic", when referring to a crystalline form of Compound (1), means that the form can comprise different chemical constituents, e.g., contain different solvent molecules in the unit cell, but have identical XRPD patterns. Isomorphic crystalline forms are sometimes referred to herein as "isomorphs".

A crystalline anhydrous form of Compound (1) described herein, e.g., Form S1 or Form S4, can undergo one or more transitions (e.g., melt or melt and crystallize into another crystalline form) at a specific temperature or across a range of temperatures. Such a specific temperature or range of temperatures can be represented by one or more endotherms (each endotherm represented by an onset temperature ($T_{onset}$)) in the crystalline form's DSC curve. In some embodiments, at such an onset temperature, a sample of a crystalline form of Compound (1) melts and undergoes a concurrently occurring side-process, e.g., crystallization or chemical decomposition. In some embodiments, at such an onset temperature, a crystalline form of Compound (1) melts in the absence of other concurrently occurring processes.

The term "characteristic peaks" when referring to the peaks in an XRPD diffraction pattern of a crystalline form of Compound (1) refers to a collection of certain peaks whose values of 2θ across a range of 0°-40° are, as a whole, uniquely assigned to one of the crystalline forms of Compound (1).

II. Crystalline (Solid) Forms of Compound (1)

In one aspect, the present invention provides crystalline forms of Compound (1), as indicated by the analytical methods set forth herein. In some embodiments, the crystalline forms of Compound (1) are anhydrous (e.g., Forms S1 and S4). Compound (1) and methods for preparing Compound (1) are disclosed in U.S. patent application publication no. US 20160083417 and PCT application publication no. WO 2014169831.

A. Form S1

The present invention provides Form S1 of Compound (1),

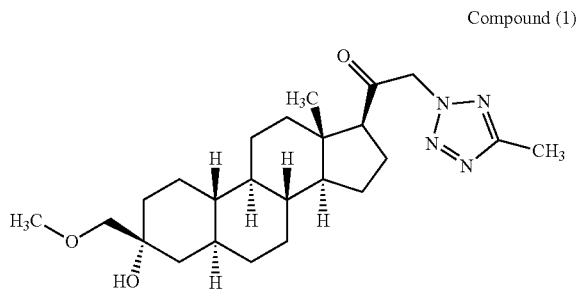

Compound (1)

which is a stable, anhydrous crystalline form of Compound (1).

In some embodiments, Form S1 is characterized by one or more peaks corresponding to 2-theta values measured in degrees of 15.4±0.3, 15.6±0.3, 18.1±0.3, 18.8±0.3, and 22.6±0.3 in an X-ray powder diffraction pattern. In other embodiments, the crystalline form is further characterized by one or more peaks corresponding to 2-theta values measured in degrees of 9.4±0.3, 11.9±0.3, 22.2±0.3, and 23.4±0.3 in an X-ray powder diffraction pattern. In some embodiments, Form S1 is characterized by peaks corresponding to 2-theta values measured in degrees of 15.4 0.3, 15.6±0.3, 18.1±0.3, 18.8±0.3, 22.6±0.3, 9.4 0.3, 11.9±0.3, 22.2±0.3, and 23.4±0.3 in an X-ray powder diffraction pattern.

In some embodiments, Form S1 is characterized by one or more peaks corresponding to 2-theta values measured in degrees of 15.4±0.2, 15.6±0.2, 18.1±0.2, 18.8±0.2, and 22.6±0.2 in an X-ray powder diffraction pattern. In other embodiments, the crystalline form is further characterized by one or more peaks corresponding to 2-theta values measured in degrees of 9.4±0.2, 11.9±0.2, 22.2±0.2, and 23.4±0.2 in an X-ray powder diffraction pattern. In some embodiments, Form S1 is characterized by peaks corresponding to 2-theta values measured in degrees of 15.4 0.2, 15.6±0.2, 18.1±0.2, 18.8±0.2, 22.6±0.2, 9.4 0.2, 11.9±0.2, 22.2±0.2, and 23.4±0.2 in an X-ray powder diffraction pattern.

And, in some embodiments, Form S1 is characterized by an X-ray powder diffraction pattern having all or substantially all the peaks presented in the XRPD pattern depicted in FIG. 1. For instance, Form S1 is characterized by an X-ray powder diffraction pattern having at least 15 (e.g., at least 20, at least 25, or at least 30) of the 33 characteristic peaks set forth in Table 2 below.

In some embodiments, Form S1 has an endotherm at a $T_{onset}$ from about 146° C. to about 157° C. (e.g., from about 147° C. to about 156° C., from about 148° C. to about 156° C., from about 149° C. to about 156° C., or from about 150° C. to about 156° C.) when heated at a rate of from about 2° C./min to about 15° C./min (e.g., from about 5° C./min to about 12° C./min, from about 7° C./min to about 10° C./min) starting at a temperature of about 30° C. In some embodiments, Form S1 has an endotherm at a $T_{onset}$ from about 146° C. to about 157° C. (e.g., from about 147° C. to about 156° C., from about 148° C. to about 156° C., from about 149° C. to about 156° C., or from about 150° C. to about 156° C.) when heated at a rate of about 10° C./min starting at a temperature of about 30° C.

In some embodiments, Form S1 is characterized by one or more peaks corresponding to 200.0±0.3 ppm, 164.3±0.3 ppm, 81.3±0.3 ppm, 70.5±0.3 ppm, and 62.2±0.3 ppm in a $^{13}C$ SSNMR spectrum. In other embodiments, crystalline Form S1 is further characterized by one or more peaks corresponding to 60.9±0.3 ppm, 60.0±0.3 ppm, 56.7±0.3 ppm, 47.8±0.3 ppm, and 45.9±0.3 ppm in a $^{13}C$ SSNMR spectrum. In some embodiments, crystalline Form S1 is further characterized by one or more peaks corresponding to 42.6±0.3 ppm, 39.3±0.3 ppm, 38.3±0.3 ppm, 35.5±0.3 ppm, 25.8±0.3 ppm, and 22.9±0.3 ppm in a $^{13}C$ SSNMR spectrum. In some embodiments, crystalline Form S1 is further characterized by one or more peaks corresponding to 200.0±0.3 ppm, 164.3±0.3 ppm, 81.3±0.3 ppm, 70.5±0.3 ppm, 62.2±0.3 ppm, 60.9±0.3 ppm, 60.0±0.3 ppm, 56.7±0.3 ppm, 47.8±0.3 ppm, and 45.9±0.3 ppm in a $^{13}C$ SSNMR spectrum. In some embodiments, crystalline Form S1 is further characterized by one or more peaks corresponding to 42.6±0.3 ppm, 39.3±0.3 ppm, 38.3±0.3 ppm, 35.5±0.3 ppm, 25.8±0.3 ppm, and 22.9±0.3 ppm in a $^{13}C$ SSNMR spectrum. In some embodiments, crystalline Form S1 is further characterized by one or more peaks corresponding to 200.0±0.3 ppm, 164.3±0.3 ppm, 81.3±0.3 ppm, 70.5±0.3 ppm, 62.2±0.3 ppm, 60.9±0.3 ppm, 60.0±0.3 ppm, 56.7±0.3 ppm, 47.8±0.3 ppm, 45.9±0.3 ppm, 42.6±0.3 ppm, 39.3±0.3 ppm, 38.3±0.3 ppm, 35.5±0.3 ppm, 25.8±0.3 ppm, and 22.9±0.3 ppm in a $^{13}C$ SSNMR spectrum. And, in some embodiments, Form S1 is characterized by a $^{13}C$ SSNMR spectrum having all or substantially all the peaks presented in FIG. 3. For instance, Form S1 is characterized by a $^{13}C$ SSNMR spectrum having at least 13 (e.g., at least 15, at least 17, at least 20, or at least 22) of the 24 characteristic peaks set forth in Table 3 below.

B. Form S4

The present invention provides Form S4 of Compound (1), which is a stable, anhydrous crystalline form of Compound (1).

In some embodiments, Form S4 is characterized by one or more peaks corresponding to 2-theta values measured in degrees of 8.9±0.3, 14.6±0.3, 16.4±0.3, 18.0±0.3, and 20.0±0.3 in an X-ray powder diffraction pattern. In other embodiments, the crystalline Form S4 is further characterized by one or more peaks corresponding to 2-theta values measured in degrees of 11.6±0.3, 15.0±0.3, 17.4±0.3, 21.2±0.3, and 29.0±0.3 in an X-ray powder diffraction pattern. In other embodiments, the crystalline Form S4 is further characterized by one or more peaks corresponding to 2-theta values measured in degrees of 9.6±0.3, 12.9±0.3, and 29.6±0.3 in an X-ray powder diffraction pattern. In some embodiments, Form S4 is characterized by peaks corresponding to 2-theta values measured in degrees of 8.9±0.3, 14.6±0.3, 16.4 0.3, 18.0 0.3, 20.0 0.3, 11.6 0.3, 15.0 0.3, 17.4±0.3, 21.2±0.3, and 29.0±0.3 in an X-ray powder diffraction pattern.

In some embodiments, Form S4 is characterized by one or more peaks corresponding to 2-theta values measured in degrees of 8.9±0.2, 14.6±0.2, 16.4±0.2, 18.0±0.2, and 20.0±0.2 in an X-ray powder diffraction pattern. In other embodiments, the crystalline Form S4 is further characterized by one or more peaks corresponding to 2-theta values measured in degrees of 11.6±0.2, 15.0±0.2, 17.4±0.2, 21.2±0.2, and 29.0±0.2 in an X-ray powder diffraction pattern. In other embodiments, the crystalline Form S4 is further characterized by one or more peaks corresponding to 2-theta values measured in degrees of 9.6±0.2, 12.9±0.2, and 29.6±0.2 in an X-ray powder diffraction pattern. In some embodiments, Form S4 is characterized by peaks corresponding to 2-theta values measured in degrees of 8.9±0.2, 14.6±0.2, 16.4 0.2, 18.0 0.2, 20.0 0.2, 11.6 0.2, 15.0 0.2, 17.4±0.2, 21.2±0.2, and 29.0±0.2 in an X-ray powder diffraction pattern.

Figure 5:
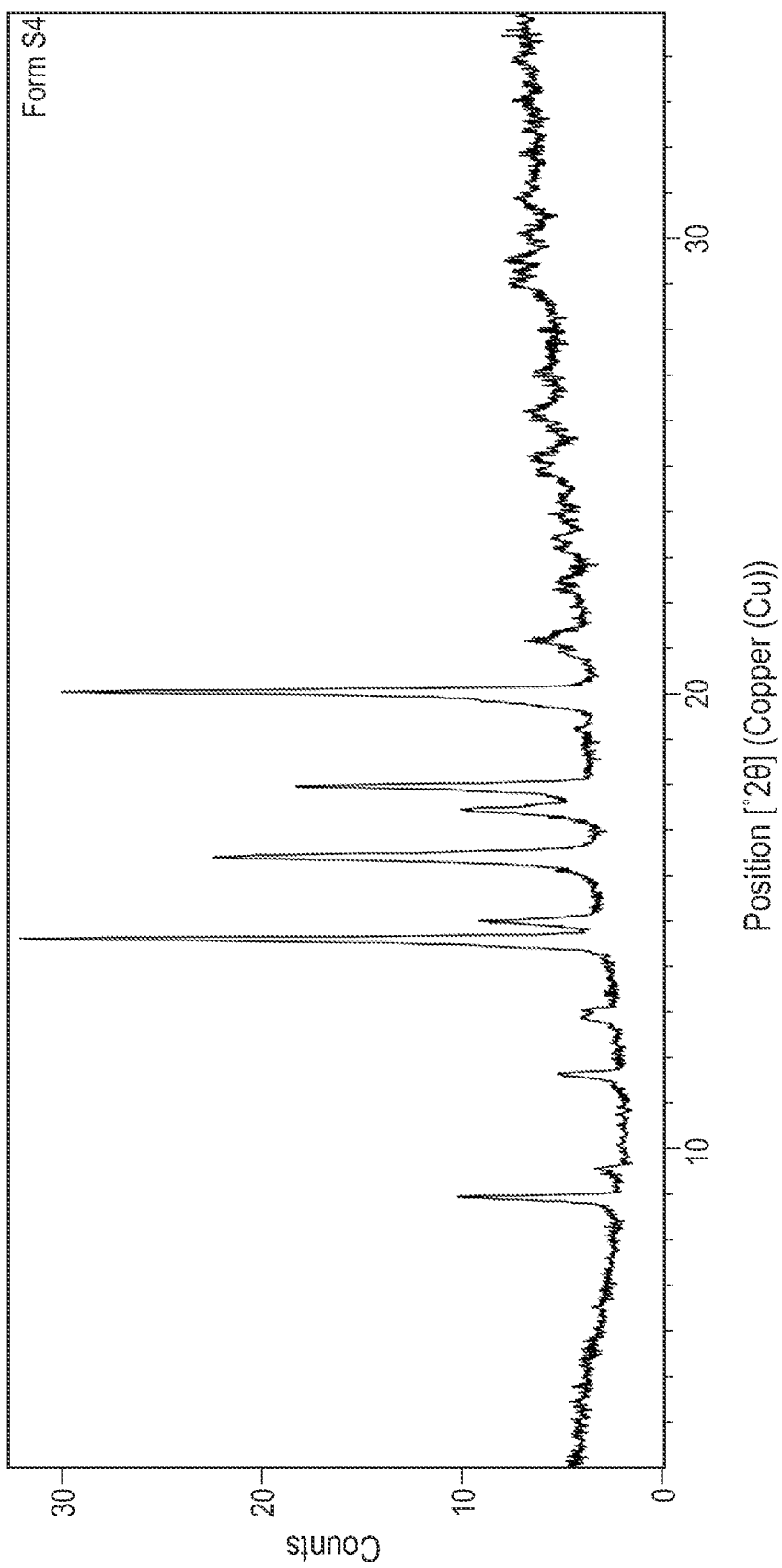
FIG. 5 depicts an exemplary XRPD pattern of Form S4 of Compound (1).

And, in some embodiments, Form S4 is characterized by an X-ray powder diffraction pattern having all or substantially all of the peaks presented in FIG. 5. For instance, Form S4 is characterized by an X-ray powder diffraction pattern having at least 15 (e.g., at least 10, at least 12, or at least 15) of the 18 characteristic peaks set forth in Table 4 below.

In some embodiments, Form S4 has an endotherm at a $T_{onset}$ from about 160° C. to about 166° C. (e.g., from about 161° C. to about 166° C., from about 162° C. to about 166° C., or from about 163° C. to about 165° C.) when heated at a rate of from about 2° C./min to about 15° C./min (e.g., from about 5° C./min to 12° C./min or from about 7° C./min to about 10° C./min) starting at a temperature of about 30° C. In some embodiments, Form S4 has an endotherm at a $T_{onset}$ from about 160° C. to about 166° C. (e.g., from about 161° C. to about 166° C., from about 162° C. to about 166° C., or from about 163° C. to about 165° C.) when heated at a rate of about 10° C./min starting at a temperature of about 30° C. And, in some embodiments, the crystalline form degrades at a temperature of about 200° C. or greater.

In some embodiments, Form S4 is characterized by one or more peaks corresponding to 200.2±0.3 ppm, 199.1±0.3 ppm, 162.8±0.3 ppm, 82.9±0.3 ppm, 82.1±0.3 ppm, and 12.6±0.3 ppm in a $^{13}C$ SSNMR spectrum. In other embodiments, the crystalline form is further characterized by one or more peaks corresponding to 70.4±0.3 ppm, 63.6±0.3 ppm, 49.7±0.3 ppm, 35.5±0.3 ppm, and 15.5±0.3 ppm in a $^{13}C$ SSNMR spectrum. In other embodiments, the crystalline form is further characterized by one or more peaks corresponding to 62.9±0.3 ppm, 61.4±0.3 ppm, 60.6±0.3 ppm, 45.4±0.3 ppm, and 37.9±0.3 ppm in a $^{13}C$ SSNMR spectrum. And, in some embodiments, Form S4 is characterized by a $^{13}C$ SSNMR spectrum having all or substantially all of the peaks presented in FIG. 9. For instance, Form S4 is characterized by a $^{13}C$ SSNMR spectrum having at least 12 (e.g., at least 15, at least 20, or at least 25) of the 34 characteristic peaks set forth in Table 5 below.

III. Methods of Generating Crystalline Forms of Compound (1)

Another aspect of the present invention provides a method of generating a crystalline anhydrous form of Compound (1) comprising (a) dissolving Compound (1) in a polar organic solvent; (b) exchanging the polar organic solvent with a non-polar organic solvent to generate a slurry; (c) heating the slurry to a temperature from about 50° C. to less than 70° C. (e.g., from about 55° C. to about 65° C.); (d) cooling the slurry to ambient temperature (e.g., from about 20° C. to about 30° C.) to form a cooled slurry; and (e) filtering crystalline Compound (1) from the cooled slurry to generate Form S1 of Compound (1).

Another aspect of the present invention provides a method of generating a crystalline anhydrous form of Compound (1) comprising (a) dissolving Compound (1) in a polar organic solvent; (b) exchanging the polar organic solvent with a non-polar organic solvent to generate a slurry; (c) heating the slurry to a temperature of 70° C. or greater; (d) cooling the slurry to ambient temperature (e.g., from about 20° C. to about 30° C.) to form a cooled slurry; and (e) filtering crystalline Compound (1) from the cooled slurry to generate Form S4 of Compound (1).

In some implementations of these methods, the exchanging step (b) comprises removing the polar organic solvent by partial vacuum distillation and addition of the non-polar solvent wherein the total volume of the mixture of solvent(s) and Compound (1) remains substantially constant (e.g., the total volume of the mixture varies no greater than about 20%, no greater than ±about 15%, no greater than ±about 10%, or no greater than about 5% during the solvent exchange).

In some implementations of these methods, the polar organic solvent comprises tetrahydrofuran, isopropyl acetate, ethyl acetate, dichloromethane, or any combination thereof.

In some implementations of these methods, the non-polar solvent comprises n-heptanes, cyclohexane, pentane, or any combination thereof.

Some implementations of these methods further comprise holding (or aging) the cooled slurry for a period of no greater than about 5 hours (e.g., no greater than about 5 hours, no greater than about 3 hours, no greater than about 2 hours, no greater than about 1 hour, or no greater than about 0.5 hours) prior to performing the filtering of step (e).

IV. Pharmaceutical Compositions

In another aspect, the invention provides a pharmaceutical composition comprising a solid form of a compound of the present invention (i.e., Compound (1)), also referred to as the "active ingredient", "active pharmaceutical ingredient", or "API", and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, topical administration, transdermal administration, intradermal administration, intrathecal administration, subcutaneous (SC) administration, intramuscular (IM) administration, sublingual/buccal, ocular, otic, vaginal, and intranasal or inhalation administration.

Generally, the solid forms of Compound (1) provided herein are administered in an effective amount. The amount of the solid forms of Compound (1) actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the solid forms of Compound (1) provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a solid form of Compound (1) or pharmaceutical composition thereof over an extended period of time, e.g., for example, over 3 months, 6 months, 1 year, 2 years, 3 years, 5 years, or the like, or may be continued indefinitely, for example, for the rest of the subject's life. In certain embodiments, the chronic administration is intended to provide a consistent level of Compound (1) in the blood or brain, e.g., within the therapeutic window over the extended period of time.

The pharmaceutical compositions of the present invention may be further delivered using a variety of dosing methods. For example, in certain embodiments, the pharmaceutical composition may be given as an injection, e.g., in order to raise the concentration of Compound (1) in the blood to an effective level. The placement of the injection dose depends on the systemic levels of the active ingredient desired throughout the body, e.g., an intramuscular or subcutaneous injection dose allows a slow release of the active ingredient.

The compositions for oral administration can take the form of bulk liquid solutions or suspensions or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, a solid form of Compound (1) is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg (e.g., from about 0.1 to about 10 mg/kg, from about 0.2 to about 5 mg/kg, from about 0.1 to about 1 mg/kg, from about 0.2 to about 0.8 mg/kg, from about 0.2 to about 0.7 mg/kg, or from about 0.2 to about 0.5 mg/kg) of a solid form of Compound (1) provided herein. In some instances, crystalline Compound (1) (e.g., Form S1 or Form S4) is administered at a dosage amount of about 10 mg to about 70 mg (e.g., about 15 mg to about 60 mg, about 25 mg to about 55 mg, or about 30 mg to about 50 mg) per oral dose per day.

Transdermal doses are generally selected to provide similar or lower blood levels than are achieved using injection doses, generally in an amount ranging from about 0.01 to about 20% by weight of, e.g., the drug reservoir or drug-adhesive reservoir for the transdermal patch, preferably from about 0.1 to about 20% by weight, preferably from about 0.1 to about 10% by weight, and more preferably from about 0.5 to about 15% by weight.

Solid compositions may include, for example, any of the following ingredients, or a solid form of Compound (1) of a similar nature: binders, surfactants, diluents or fillers, buffering agents, anti-adherents, glidants, hydrophilic or hydrophobic polymers, retardants (e.g., delayed release agents), stabilizing agents or stabilizers, disintegrants or superdisintegrants, dispersants, antioxidants, antifoaming agents, fillers, flavors, colorants, lubricants, sorbents, preservatives, plasticizers, coatings, or sweeteners, or mixtures thereof. For example, the excipient or excipients could be a binder such as microcrystalline cellulose, polyvinyl pyrrolidone, hydroxypropyl cellulose, low viscosity hydroxypropyl methylcellulose, gum tragacanth or gelatin; a diluent such as mannitol, microcrystalline cellulose, maltodextrin, starch or lactose, a disintegrating agent such as alginic acid, sodium starch glycolate (e.g., Primogel), croscarmellose sodium, crospovidone, or corn starch; a lubricant such as magnesium stearate, sodium stearyl fumarate or glyceryl behenate; a glidant such as colloidal silicon dioxide or talc; a preservative such as potassium sorbate or methyl paraben, a surfactant, such as sodium lauryl sulfate, docusate sodium, poysorbate 20, polysorbate 80, cetyl triethyl ammonium bromide, polyethyelene oxide-polypropylene oxide copolymers, or Cremophor EL, an antioxidant such as butylhydroxy toluene, butyl hydroxyanisole, propyl gallate, ascorbic acid, citric acid, tocopherol or tocopherol acetate, sodium sulfite, or sodium metabisulfite, a coating comprising one or more of hydroxypropylmethylcellulose, polyvinyl alcohol, acrylate copolymers, cellulose acetate, ethyl acetate, hydroxypropylmethylcellulose acetate succinate, shellac and others, a sweetening agent such as sucrose, sucralose, acesulfame K, sodium aspartame or saccharin; or a flavoring agent such as peppermint, methyl salicylate, cherry, grape, lemon, or orange flavoring. Any of the well known pharmaceutical excipients may be incorporated in the dosage form and may be found in the FDA's Inactive Ingredients Guide, Remington: The Science and Practice of Pharmacy, Twenty-first Ed., (Pharmaceutical Press, 2005); Handbook of Pharmaceutical Excipients, Sixth Ed. (Pharmaceutical Press, 2009) all of which are incorporated by reference.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration and stability of the active ingredients or Formulation. All such known transdermal formulations and ingredients are included within the scope provided herein. Topical delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols, sticks, and patches.

The solid forms of Compound (1) provided herein can also be administered by a transdermal device. Accordingly, transdermal administration can be accomplished using a patch either of the reservoir or membrane type, or of an adhesive matrix or other matrix variety. Delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols, sticks, and patches. For a transdermal patch, the active agent layer includes one or more active agents, one of which is Compound (1). In certain embodiments, the matrix is an adhesive matrix. The matrix may include polymeric materials. Suitable polymers for the adhesive matrix include, but are not limited to: polyurethanes, acrylates, styrenic block copolymers, silicones, and the like. For example, the adhesive matrix may include, but is not limited to, an acrylate polymer, polysiloxanes, polyisobutylene (PIB), polyisoprene, polybutadiene, styrenic block polymers, combinations of thereof, and the like. Additional examples of adhesives are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference.

In certain embodiments, the active agent layer includes a permeation enhancer. The permeation enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g., —OCH$_2$CH$_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (e.g., fatty acid esters of glycerol), such as but not limited to glycerol esters of fatty acids having 6 to 18 carbon atoms, diglycerides, triglycerides or combinations thereof. In some embodiments, the polymer matrix includes a polyvinylpyrrolidone. The composition may further include one or more fillers or one or more antioxidants. In some embodiments, the transdermal formulations described may have a multi-layer structure. For example, the transdermal formulation may have an adhesive matrix and a backing.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

A solid form of Compound (1) of the present invention can also be administered in sustained release forms or from sustained release drug delivery systems. A description of representative sustained release materials can be found in Remington's Pharmaceutical Sciences.

V. Methods of Use and Treatments

In an alternative embodiment, the crystalline forms of Compound (1) may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the solid form of Compound (1).

A. Pharmaceutical Compositions

In one aspect, provided herein is a pharmaceutical composition comprising a solid form of Compound (1) described herein (e.g., Form S1 or Form S4), and a pharmaceutically acceptable excipient. In certain embodiments, the solid form of Compound (1) is provided in an effective amount in the pharmaceutical composition. In certain embodiments, the solid form of Compound (1) is provided in a therapeutically effective amount.

In certain embodiments, the pharmaceutical composition comprises an effective amount of the active ingredient. In certain embodiments, the pharmaceutical composition comprises a therapeutically effective amount of the active ingredient.

The pharmaceutical compositions provided herein can be administered by a variety of routes including, but not limited to, oral (enteral) administration, parenteral (by injection) administration, rectal administration, vaginal administration, transdermal administration, intradermal administration, intrathecal administration, subcutaneous (SC) administration, intravenous (IV) administration, intramuscular (IM) administration, and intranasal administration.

Generally, the solid forms of Compound (1) provided herein are administered in an effective amount. The amount of the solid form of Compound (1) actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration").

Chronic administration refers to administration of a compound or pharmaceutical composition thereof over an extended period of time, e.g., for example, over 3 months, 6 months, 1 year, 2 years, 3 years, 5 years, or the like, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration or stability of the active ingredients or formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions, which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions that are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21st ed., Lippincott Williams & Wilkins, 2005.

One aspect provides a kit comprising a composition (e.g., a solid composition) comprising a crystalline form (e.g., Form S1, Form S4, or any combination thereof) of Compound (1).

B. Combination Therapy

A crystalline form (e.g., Form S1, Form S4, or any combination thereof) of Compound (1) may be administered in combination with an additional agent or therapy. A subject to be administered a compound disclosed herein may have a disease, disorder, or condition, or a symptom thereof, that would benefit from treatment with another agent or therapy. Combination therapy may be achieved by administering two or more agents, each of which is formulated and administered separately, or by administering two or more agents in a single formulation. In some embodiments, the two or more agents in the combination therapy can be administered simultaneously. In other embodiments, the two or more agents in the combination therapy are administered separately. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc. Exemplary additional agents are described below.

1. Selective Serotonin Reuptake Inhibitor (SSRI)

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with an SSRI(s). SSRIs include antidepressants that increase the level of serotonin in the brain. Exemplary SSRIs include, but are not limited to, Citalopram (Celexa), Escitalopram (Lexapro), Fluoxetine (Prozac), Fluvoxamine (Luvox), Paroxetine (Paxil), and Sertraline (Zoloft).

2. MAO Inhibitor (MAOI)

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with an MAOI(s). MAOIs include antidepressants that inhibit monoamine oxidase activity in the brain. Exemplary MAOIs include, but are not limited to, Isocarboxazid (Marplan), Phenelzine (Nardil), Selegiline (Emsam), and Tranylcypromine (pamate).

3. Norepinephrine Reuptake Inhibitor (NERI)

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with an NERI(s). Exemplary NERIs include, but are not limited to, Atomoxetine (Strattera), Reboxetine (Edronax, Vestra), Bupropion (Wellbutrin, Zyban), Duloxetine, Desipramine (Norpramin), Amedalin (UK-3540-1), Daledalin (UK-3557-15), Edivoxetine (LY-2216684), Esreboxetine, Lortalamine (LM-1404), Nisoxetine (LY-94,939), Talopram (tasulopram) (Lu 3-010), Talsupram (Lu 5-005), Tandamine (AY-23,946), and Viloxazine (Vivalan).

4. Antipsychotics

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with an antipsychotic agent(s). Antipsychotics include D2 antagonists, lowering dopaminergic neurotransmission in the dopamine pathways. Exemplary antipsychotics include, but are not limited to, Asenapine (Saphris), Aripiprazole (Abilify), Cariprazine (Vrayar), Clozapine (Clozaril), Droperidol, Fluperlapine, Mesoridazine, Quetiapine Hemifumarate, Raclopride, Spiperone, Sulpiride, Trimethobenzamide hydrochloride, Trifluoperazine Dihydrochloride, lurasidone (Latuda), Olanzapine (Zyprexa), Quetiapine (Seroquel), Zotepine, Risperidone (Risperdal), Ziprasidone (Geodon), Mesotidazine, Chlorpromazine hydrochloride, and Haloperidol (Haldol).

5. Cannabinoids

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with a cannabinoid(s). Exemplary cannabinoids include, but are not limited to, Cannabidiol (Epidiolex), Tetrahydrocannabinolic Acid, Tetrahydrocannabinol, Cannabidolic Acid, Cannabinol, Cannabigerol, Cannabichromene, Tetrahydrocannabivarin, and Cannabidivarin.

6. NMDA Receptor Antagonists

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with an NMDA receptor antagonist(s). NMDA receptor antagonists are a class of drugs that inhibit the action of the N-methyl-d-aspartate receptor. Exemplary NMDA antagonists include, but are not limited to, Ketamine, Esketamine, Ketobemidone, Ifendopril, 5,7-Dichlorokynurenic Acid, Licostinel, Memantine, Gavestinel, Phencyclidine, Dextromethorphan, Remacemide, Selfotel, Tiletamine, Dextropropoxyphene, Aptiganel, Dexanabinol, and Amantadine. NMDA receptor antagonists also include opioids such as Methadone, Dextropropoxyphene, Pethidine, Levorphanol, Tramadol, Neramexane, and Ketobemidone.

7. GABA Receptor Agonists

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with GABA receptor agonist(s) (e.g., $GABA_A$ receptor agonists). GABA receptor agonist is a class of drugs or compounds that are agonists for one or more of the GABA receptors. Exemplary GABA receptor agonists include, but are not limited to, Clobazam, Topiramate, Muscimol, Progabide, Riluzole, Baclofen, Gabapentin, Vigabatrin, Valproic Acid, Tiagabine, Lamotrigine, Pregabalin, Phenyloin, Carbamazepine, Thiopental, Thiamylal, Pentobarbital, Secobarbital, Hexobarbital, Butobarbital, Amobarbital, Barbital, Mephobarbital, Phenobarbital, Primidone, Midazolam, Triazolam, Lometazepam, Flutazolam, Nitrazepam, Fluritrazepam, Nimetazepam, Diazepam, Medazepam, Oxazolam, Prazeam, Tofisopam, Rilmazafonoe, Lorazepam, Temazepam, Oxazepam, Fluidazepam, Chlordizaepoxide, Cloxazolam, Flutoprazepam, Alprazolam, Estazolam, Bromazepam, Flurazepam, Clorazepate Potassium, Haloxazolam, Ethyl Loflazepate, Qazepam, Clonazepam, Mexazolam, Etizolam, Brotizolam, Clotizaepam, Propofol, Fospropofol, Zolpidem, Zopiclone, Exzopiclone, Muscimol, TFQP/gaboxadol, Isoguvacine, Kojic amine, GABA, Homotaurine, Homohypotaurine, Trans-aminocyclopentane-3-carboxylic acid, Trans-amino-4-crotonic acid, b-guanidinopropionic acid, homo-b-proline, Isonipecotic acid, 3-((aminoiminomethyl)thio)-2-propenoic acid (ZAP A), Imidazoleacetic acid, and Piperidine-4-sulfonic acid (P4S).

8. Cholinesterase Inhibitors

In some embodiments, a crystalline form (e.g., Form S1, Form S4, or any combination thereof) of Compound (1), or a composition comprising a crystalline form (e.g., Form S1, Form S4, or any combination thereof) of Compound (1) is administered in combination with a cholinesterase inhibitor(s). In general, cholinergics are compounds which mimic the action of acetylcholine and/or butyrylcholine. Cholinesterase inhibitors are a class of drugs that prevent the breakdown of acetylcholine. Exemplary cholinesterase inhibitors include, but are not limited to, Donepizil (Aricept), Tacrine (Cognex), Rivastigmine (Exelon, Exelon Patch), Galantamine (Razadyne, Reminyl), Memantine/Donepezil (Namzaric), Ambenonium (Mytelase), Neostigmine (Bloxiverz), Pyridostigmine (Mestinon Timespan, Regonol), and Galantamine (Razadyne).

The present disclosure also contemplates, among other things, administration of a crystalline form (e.g., Form S1, Form S4, or any combination thereof) of Compound (1), or a composition comprising a crystalline form (e.g., Form S1, Form S4, or any combination thereof) of Compound (1) to a subject has been previously administered an agent selected from the group consisting of a bronchial muscle/airway relaxant, an antiviral, oxygen, an antibody, and an antibacterial. In some embodiments an additional agent is administered to a subject prior to administration of a crystalline form (e.g., Form S1, Form S4, or any combination thereof) of Compound (1), or a composition comprising a crystalline form (e.g., Form S1, Form S4, or any combination thereof) of Compound (1) and an additional agent is selected from the group consisting of a bronchial muscle/airway relaxant, an antiviral, oxygen, an antibody, and an antibacterial. In some embodiments, a crystalline form (e.g., Form S1, Form S4, or any combination thereof) of Compound (1), or a composition comprising a crystalline form (e.g., Form S1, Form S4, or any combination thereof) of Compound (1) is co-administered with an agent selected from a bronchial muscle/airway relaxant, an antiviral, oxygen, and an antibacterial to a subject.

C. Methods of Use and Treatment

In an aspect, a crystalline form (e.g., Form S1, Form S4, or any combination thereof) of Compound (1), or a composition comprising a crystalline form (e.g., Form S1, Form S4, or any combination thereof) of Compound (1) is envisioned to be useful as one or more therapeutic agents for treating a CNS-related disorder (e.g., a sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need thereof (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression (e.g., major depressive disorder (MDD)), dysthymic disorder (e.g., mild depression), bipolar disorder (e.g., I and/or II), anxiety disorders (e.g., generalized anxiety disorder (GAD), social anxiety disorder), treatment resistant depression (TRD), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder.

In an aspect, provided is a method of alleviating or preventing seizure activity in a subject, comprising administering to the subject in need of such treatment an effective amount of a crystalline form (e.g., Form S1, Form S4, or any combination thereof) of Compound (1). In some embodiments, the method alleviates or prevents epileptogenesis.

In yet another aspect, provided is a combination of a crystalline form (e.g., Form S1, Form S4, or any combination thereof) of Compound (1) and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a crystalline form (e.g., Form S1, Form S4, or any combination thereof) of Compound (1) to the subject.

In yet another aspect, provided is a method of treating or preventing stress or anxiety in a subject, comprising administering to the subject in need of such treatment an effective amount of a crystalline form (e.g., Form S1, Form S4, or any combination thereof) of Compound (1), or a pharmaceutical composition thereof.

In yet another aspect, provided is a method of alleviating or preventing insomnia in a subject, comprising administering to the subject in need of such treatment an effective amount of a crystalline form (e.g., Form S1, Form S4, or any combination thereof) of Compound (1), or a pharmaceutical composition thereof.

In yet another aspect, provided is a method of inducing sleep and maintaining substantially the level of REM sleep that is found in normal sleep, wherein substantial rebound insomnia is not induced, comprising administering an effective amount of a crystalline form (e.g., Form S1, Form S4, or any combination thereof) of Compound (1).

In yet another aspect, provided is a method of alleviating or preventing premenstrual syndrome (PMS) or postnatal depression (PND) in a subject, comprising administering to the subject in need of such treatment an effective amount of a crystalline form (e.g., Form S1, Form S4, or any combination thereof) of Compound (1).

In yet another aspect, provided is a method of treating or preventing mood disorders in a subject, comprising administering to the subject in need of such treatment an effective amount of a crystalline form (e.g., Form S1, Form S4, or any combination thereof) of Compound (1). In certain embodiments the mood disorder is depression.

In yet another aspect, provided is a method of cognition enhancement or treating memory disorder by administering to the subject a therapeutically effective amount of a crystalline form (e.g., Form S1, Form S4, or any combination thereof) of Compound (1). In certain embodiments, the disorder is Alzheimer's disease. In certain embodiments, the disorder is Rett syndrome.

In yet another aspect, provided is a method of treating attention disorders by administering to the subject a therapeutically effective amount of a crystalline form (e.g., Form S1, Form S4, or any combination thereof) of Compound (1). In certain embodiments, the attention disorder is ADHD.

Inflammation of the central nervous system (CNS) (neuroinflammation) is recognized to be a feature of all neurological disorders. Major inflammatory neurological disorders include multiple sclerosis (characterized by an immune-mediated response against myelin proteins), and meningoencephalitis (where infectious agents triggered the inflammatory response). Additional scientific evidence suggests a potential role of inflammatory mechanisms in other neurological conditions such as Alzheimer's disease, Parkinson's disease, Huntington' disease, amyotrophic lateral sclerosis, stroke and traumatic brain injuries. In one embodiment, a crystalline form (e.g., Form S1, Form S4, or any combination thereof) of Compound (1) is useful in treating neuroinflammation. In another embodiment, the crystalline forms of the present invention are useful in treating inflammation in neurological conditions, including Alzheimer's disease, Parkinson's disease, Huntington's disease, amyotrophic lateral sclerosis, stroke, and traumatic brain injuries.

In certain embodiments, the crystalline form (e.g., Form S1, Form S4, or any combination thereof) of Compound (1) is administered to the subject chronically. In certain embodiments, the compound is administered to the subject orally, subcutaneously, intramuscularly, or intravenously.

1. Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

2. Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

3. Mood Disorders

Also provided herein are methods for treating a mood disorder, for example clinical depression, postnatal depression or postpartum depression, perinatal depression, atypical depression, melancholic depression, psychotic major depression, cataonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method comprises monitoring a subject with a known depression scale, e.g., the Hamilton Depression (HAM-D) scale, the Clinical Global Impression-Improvement Scale (CGI), and the Montgomery-Asberg Depression Rating Scale (MADRS). In some embodiments, a therapeutic effect can be determined by reduction in Hamilton Depression (HAM-D) total score exhibited by the subject. Reduction in the HAM-D total score can happen within 4, 3, 2, or 1 days; or 96, 84, 72, 60, 48, 24, 20, 16, 12, 10, 8 hours or less. The therapeutic effect can be assessed across a specified treatment period. For example, the therapeutic effect can be determined by a decrease from baseline in HAM-D total score after administering a crystalline form (e.g., Form S1, Form S4, or any combination thereof) of Compound (1) (e.g., 12, 24, or 48 hours after administration;

or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a crystalline form (e.g., Form S1, Form S4, or any combination thereof) of Compound (1)) is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a crystalline form (e.g., Form S1, Form S4, or any combination thereof) of Compound (1) is greater than or equal to 23. In some embodiments, the baseline score is at least 10, 15, or 20. In some embodiments, the HAM-D total score of the subject after treatment with a crystalline form (e.g., Form S1, Form S4, or any combination thereof) of Compound (1) is about 0 to 10 (e.g., less than 10; 0 to 10, 0 to 6, 0 to 4, 0 to 3, 0 to 2, or 1.8). In some embodiments, the HAM-D total score after treatment with a crystalline form (e.g., Form S1, Form S4, or any combination thereof) of Compound (1) is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a crystalline form (e.g., Form S1, Form S4, or any combination thereof) of Compound (1). In some embodiments, the decrease in the baseline HAM-D total score to HAM-D total score after treatment with a crystalline form (e.g., Form S1, Form S4, or any combination thereof) of Compound (1) is at least 1, 2, 3, 4, 5, 7, 10, 25, 40, 50, or 100 fold. In some embodiments, the percentage decrease in the baseline HAM-D total score to HAM-D total score after treatment with a crystalline form (e.g., Form S1, Form S4, or any combination thereof) of Compound (1) is at least 50% (e.g., 60%, 70%, 80%, or 90%). In some embodiments, the therapeutic effect is measured as a decrease in the HAM-D total score after treatment with a crystalline form (e.g., Form S1, Form S4, or any combination thereof) of Compound (1) relative to the baseline HAM-D total score (e.g., 12, 24, 48 hours after administration; or 24, 48, 72, 96 hours or more; or 1 day, 2 days, 14 days, or more) is at least 10, 15, or 20 points.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a crystalline form (e.g., Form S1, Form S4, or any combination thereof) of Compound (1). In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a crystalline form (e.g., Form S1, Form S4, or any combination thereof) of Compound (1). In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a crystalline form (e.g., Form S1, Form S4, or any combination thereof) of Compound (1). In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a crystalline form (e.g., Form S1, Form S4, or any combination thereof) of Compound (1). In some embodiments, the therapeutic effect is a decrease from baseline in HAM-D total score after treatment with a crystalline form (e.g., Form S1, Form S4, or any combination thereof) of Compound (1) once a day for 14 days. In some embodiments, the HAM-D total score of the subject before treatment with a crystalline form (e.g., Form S1, Form S4, or any combination thereof) of Compound (1) is at least 24. In some embodiments, the HAM-D total score of the subject before treatment with a crystalline form (e.g., Form S1, Form S4, or any combination thereof) of Compound (1) is at least 18. In some embodiments, the HAM-D total score of the subject before treatment with a crystalline form (e.g., Form S1, Form S4, or any combination thereof) of Compound (1) is between and including 14 and 18. In some embodiments, the decrease in HAM-D total score after treating the subject with a crystalline form (e.g., Form S1, Form S4, or any combination thereof) of Compound (1) relative to the baseline HAM-D total score is at least 10. In some embodiments, the decrease in HAM-D total score after treating the subject with a crystalline form (e.g., Form S1, Form S4, or any combination thereof) of Compound (1) relative to the baseline HAM-D total score is at least 15 (e.g., at least 17). In some embodiments, the HAM-D total score associated with treating the subject with a crystalline form (e.g., Form S1, Form S4, or any combination thereof) of Compound (1) is no more than a number ranging from 6 to 8. In some embodiments, the HAM-D total score associated with treating the subject with a crystalline form (e.g., Form S1, Form S4, or any combination thereof) of Compound (1) is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., a major depressive disorder. In some embodiments, the method of treating the depressive disorder, e.g., the major depressive disorder, provides a therapeutic effect within the second day of the treatment period. In some embodiments, the therapeutic effect is a decrease from baseline in CGI score at the end of a treatment period (e.g., 14 days after administration).

In some embodiments, the method provides therapeutic effect (e.g., as measured by reduction in Montgomery-Asberg Depression Rating Scale (MADRS)) within 14, 10, 4, 3, 2, or 1 days, or 24, 20, 16, 12, 10, or 8 hours or less. In some embodiments, the CNS-disorder is a depressive disorder, e.g., a major depressive disorder. In some embodiments, the method of treating the depressive disorder, e.g., the major depressive disorder, provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Asberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Asberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is an improvement measured by the EPDS.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

4. Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e., extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

5. Women's Health Disorders

Provided herein are methods for treating conditions or disorders related to women's health. Conditions or disorders related to women's health include, but are not limited to, gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

6. Epilepsy

The crystalline forms (e.g., Form S1, Form S4, or any combination thereof) of Compound (1), or a pharmaceutically acceptable composition thereof, can be used in a method described herein, for example in the treatment of a disorder described herein such as epilepsy, status epilepticus, or seizure.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

7. Epileptogenesis

The crystalline forms (e.g., Form S1, Form S4, or any combination thereof) of Compound (1) and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

8. Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The crystalline forms (e.g., Form S1, Form S4, or any combination thereof) of Compound (1), or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

9. Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

10. Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

The methods described herein can be used to treat tremor, for example a crystalline form (e.g., Form S1, Form S4, or any combination thereof) of Compound (1) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, or disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occur irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

11. Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Also described herein are methods of ameliorating one or more symptoms of a respiratory condition in a subject, comprising administering to the subject an effective amount of a crystalline form (e.g., Form S1, Form S4, or any combination thereof) of Compound (1) or a pharmaceutical composition described herein.

In one aspect, provided herein is a method of treating a subject wherein the subject exhibits one or more symptoms of a respiratory condition and/or has been diagnosed with a respiratory condition, comprising administering to said subject an effective amount of a crystalline form (e.g., Form S1, Form S4, or any combination thereof) of Compound (1), or a composition comprising a crystalline form (e.g., Form S1, Form S4, or any combination thereof) of Compound (1).

In some embodiments, the present disclosure contemplates a method of treating a subject comprising administering to said subject a crystalline form (e.g., Form S1, Form S4, or any combination thereof) of Compound (1) or a composition comprising a crystalline form (e.g., Form S1, Form S4, or any combination thereof) of Compound (1), wherein the subject has a respiratory condition.

In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, may result in the reduction of the severity of one or more symptoms of a respiratory condition or retard or slow the progression of one or more symptoms of a respiratory condition.

In some embodiments, a subject with a respiratory condition has been or is being treated with mechanical ventilation or oxygen. In some embodiments, a subject with a respiratory condition has been or is being treated with mechanical ventilation.

In some embodiments, a crystalline form (e.g., Form S1, Form S4, or any combination thereof) of Compound (1) or a composition comprising a crystalline form (e.g., Form S1, Form S4, or any combination thereof) of Compound (1) is administered to a subject that is being or has been treated with mechanical ventilation. In some embodiments, administration of a crystalline form (e.g., Form S1, Form S4, or any combination thereof) of Compound (1) or a composition comprising a crystalline form (e.g., Form S1, Form S4, or any combination thereof) of Compound (1) continues throughout a subject's treatment with mechanical ventilation. In some embodiments, administration of a crystalline form (e.g., Form S1, Form S4, or any combination thereof) of Compound (1) or a composition comprising a crystalline form (e.g., Form S1, Form S4, or any combination thereof) of Compound (1) continues after a subject has ended treatment with mechanical ventilation.

In some embodiments, a crystalline form (e.g., Form S1, Form S4, or any combination thereof) of Compound (1) or a composition comprising a crystalline form (e.g., Form S1, Form S4, or any combination thereof) of Compound (1) is administered to a subject who is receiving or has received treatment with a sedative. In some embodiments, a sedative is propofol or a benzodiazepine.

In some embodiments, the present disclosure includes administering to a subject in need thereof a crystalline form (e.g., Form S1, Form S4, or any combination thereof) of Compound (1) or a composition comprising a crystalline form (e.g., Form S1, Form S4, or any combination thereof) of Compound (1) in an amount sufficient to increase oxygen saturation in blood. In some embodiments, oxygen saturation in blood is measured using pulse oximetry.

In some embodiments, the present disclosure contemplates a method of treating a cytokine storm in a patient. In some embodiments a method of treating a cytokine storm comprising the step of administering to the patient a crystalline form (e.g., Form S1, Form S4, or any combination thereof) of Compound (1) or a crystalline form (e.g., Form S1, Form S4, or any combination thereof) of Compound (1). In some embodiments, a symptom of a cytokine storm is lung inflammation. In some embodiments, a patient undergoing a cytokine storm has acute respiratory distress syndrome (ARDS).

12. Respiratory Condition

In some embodiments, a subject with a respiratory condition suffers from respiratory distress. In some embodiments, respiratory distress includes acute respiratory distress.

In some embodiments, a subject with a respiratory condition may exhibit one or more symptoms selected from the group consisting of airway hyper-responsiveness, inflammation of lung tissue, lung hypersensitivity, and inflammation-related pulmonary pain.

In some embodiments a subject with a respiratory condition may exhibit inflammation of lung tissue. In some embodiments, inflammation of lung tissue is bronchitis or bronchiectasis. In some embodiments, inflammation of lung tissue is pneumonia. In some embodiments, pneumonia is ventilator-associated pneumonia or hospital-acquired pneumonia. In some embodiments, pneumonia is ventilator-associated pneumonia.

In some embodiments, administration of the crystalline form (e.g., Form S1, Form S4, or any combination thereof) of Compound (1) or pharmaceutical composition thereof to a subject exhibiting symptoms of a respiratory condition, results in reduction of the severity of respiratory distress in a subject with a respiratory condition or retard or slow the progression of respiratory distress in a subject with a respiratory condition.

In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, results in reduction of the severity of airway hyper-responsiveness in a subject with a disease associated with a coronavirus or retard or slow the progression of airway hyper-responsiveness in a subject with a respiratory condition.

In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, results in reduction of the severity of inflammation of lung tissue in a subject with a respiratory condition or retard or slow the progression of inflammation of lung tissue in a subject with a respiratory condition. In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, results in reduction of the severity of pneumonia in a subject with a respiratory condition or retard or slow the progression of pneumonia in a subject with a respiratory condition.

In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, results in reduction of the severity of lung hypersensitivity in a subject with a respiratory condition or retard or slow the progression of lung hypersensitivity in a subject with a respiratory condition.

In some embodiments, administration of a crystalline form (e.g., Form S1, Form S4, or any combination thereof) of Compound (1) or a composition comprising a crystalline form (e.g., Form S1, Form S4, or any combination thereof) of Compound (1) to a subject exhibiting symptoms of a respiratory condition, results in reduction of the severity of inflammation-related pulmonary pain in a subject with a respiratory condition or retard or slow the progression of inflammation-related pulmonary pain in a subject with a respiratory condition.

In some embodiments, a subject with a respiratory condition is undergoing or has undergone treatment for an infection, fibrosis, a fibrotic episode, chronic obstructive pulmonary disease, Sarcoidosis (or pulmonary sarcoidosis) or asthma/asthma-related inflammation.

In some embodiments, a subject exhibits symptoms of and/or has been diagnosed with asthma. In some embodiments, a subject is or has undergone an asthmatic attack.

In some embodiments, a subject is undergoing or has undergone treatment for fibrosis or a fibrotic episode. In some embodiments, the fibrosis is cystic fibrosis.

In some embodiments, a respiratory condition is the result of and/or related to a disease or condition selected from the group consisting of cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, pulmonary sarcoidosis, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington, spinocerebellar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

13. Infections

The present disclosure contemplates, among other things, treatment of a subject who has an infection. The present disclosure contemplates, among other things, treatment of a subject who has a disease associated with an infection. In some embodiments, an infection is a viral infection or a bacterial infection. In some embodiments, an infection is a viral infection. In some embodiments, an infection is a bacterial infection.

In some embodiments, a viral infection is an infection of a virus selected from the group consisting of a coronavirus, an influenza virus, human rhinovirus, a human parainfluenza virus, human metapneumovirus and a hantavirus. In some embodiments, a virus is a coronavirus. In some embodiments, a coronavirus is selected from the group consisting of SARS-CoV, SARS-CoV-2, and MERS-CoV.

The present disclosure contemplates, among other things, treatment of a subject who has a disease associated with coronavirus. In some embodiments, a disease associated with a coronavirus is selected from the group consisting of coronavirus disease 2019 (COVID-19), severe acute respiratory syndrome (SARS) and Middle East respiratory syndrome (MERS). In some embodiments, a disease associated with a coronavirus is selected from the group consisting of COVID-19. In some embodiments, a coronavirus is selected from a group consisting of SARS-CoV-1, SARS-CoV-2, and 2012-nCoV. In some embodiments, a coronavirus is SARS-CoV-2.

In some embodiments, a bacterial infection is an infection of a bacteria selected from the group consisting of *Streptococcus pneumoniae, Chlamydia pneumoniae, Staphylococcus aureus, Pseudomonas aeruginosa,* and *Haemophilus influenzae*. In some embodiments, *Staphylococcus aureus* is methicillin-resistant *Staphylococcus aureus*.

VI. Examples

In order that the invention described herein may be more fully understood, the following examples are set forth. The examples described in this application are offered to illustrate the crystalline solid forms provided herein and are not to be construed in any way as limiting their scope.

General Analytical Methods.

Unless stated otherwise herein, the following analytical methods were followed in the analysis and characterization of solid (i.e., crystalline) forms of Compound (1).

A. XRPD Analyses.

XRPD analyses were performed using a PANalytical X'pert pro with PIXcel detector (128 channels), scanning the samples between 3 and 35° 2θ. Solid Compound (1) was gently ground to release any agglomerates and loaded onto a multi-well plate with a Mylar polymer film to support the sample. The multi-well plate was then placed into the diffractometer and analyzed using Cu K radiation (α1λ=1.54060 Å; α2=1.54443 Å; β=1.39225 Å; α1α2 ratio=0.5) running in transmission mode (step size 0.0130° 2θ, step time 18.87 s) using 40 kV/40 mA generator settings. Data were visualized and images generated using the HighScore Plus 4.7 desktop application (PANalytical, 2017). The 2θ position was calibrated using alumina powder reference standard on a monthly basis.

B. TGA/DSC Analyses.

TGA data were collected using a TA Q500 TGA from TA Instruments, and DSC was conducted using a TA Q2000 DSC from TA Instruments. TGA and DSC operating parameters are provided in Table 1. The TGA was calibrated with a nickel reference standard and the DSC was calibrated with an indium reference standard.

TABLE 1

Parameters for TGA and DSC analyses.

| Parameter | TGA | DSC |
| --- | --- | --- |
| Method | Ramp | Ramp |
| Sample Pan | Platinum, open | Aluminum, crimped |
| Temperature | RT—desired temperature | 25° C.—desired temperature |
| Heating Rate | 10° C./min | 10° C./min or 20° C./min* |
| Purge gas | $N_2$ | $N_2$ |

*A faster heating rate (20° C./min) was used in order to increase the sensitivity of weak thermal transitions in transition temperature determination DSC experiments.

C. $^{13}C$ Solid State NMR Analyses.

Solid-state NMR (SSNMR) experiments were performed on a Bruker Avance I spectrometer (Bruker, Billerica, MA) operating at 100.51 MHz for $^{13}C$ and 399.67 MHz for $^1H$. A Chemagnetics APEX probe, refitted with a 7 mm magic angle spinning module (Revolution NMR, Fort Collins, CO) was used to acquire the data. Each sample was packed into a 7 mm zirconia rotor. Magic angle spinning speeds were 5 kHz. $^{13}$C chemical shifts are reported relative to the methyl peak of 3-methylglutaric acid at 18.84 ppm with an accuracy of ±0.4 ppm.

Saturation recovery was used to measure $^1$H T$_1$ relaxation times. $^{13}$C spectra were collected using a pre-saturation period ($^1$H p/2, no delay, loop 1×), variable delay list, $^1$H p/2 pulse, and then the cross polarization total suppression of spinning sidebands (CPTOSS) sequence, and ~63.3 kHz (3.95 ms $^1$H p/2)$^1$H SPINAL-64 decoupling. T1guide in the Bruker Topspin 2.1 patch level 6 software package was used to determine the $^1$H T1 values of the samples. High quality $^{13}$C CPTOSS spectra were acquired at 5 kHz MAS using the CPTOSS sequence, 624 acquisitions, 20 second pulse delay, a 1.5 ms contact time, 3994 acquisition points (-50 ms acquisition time) and approximately 3.46 hours of experimental time. Data collection was done at a nominal temperature of 18.5° C. Data was processed in the Topsin software.

E. Dynamic Vapor Sorption (DVS) Analyses.

Approximately 10-20 mg of sample was placed into a mesh vapor sorption balance pan and loaded into a DVS Intrinsic/Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained. The microbalance was calibrated monthly using a certified calibration weight and the relative humidity at 25° C. was calibrated against deliquescence point of LiCl, MgCl and NaCl. Data were not corrected for the initial water content of the sample, and data were shown according to the dry mass of the sample at 0% RH.

Example No. 1: Preparation of Form S1 of Compound (1)

Method 1.

Crude Compound (1) (431 g) is dissolved in tetrahydrofuran (3500 mL) with stirring under nitrogen. The solvent is exchanged by adding n-heptane (6500 mL) slowly while distilling under partial vacuum, keeping the temperature of the contents ≤40° C., and maintaining the volume in the vessel at approximately 3500 mL. Compound (1) begins to crystallize during the distillation. At the end of the distillation, the vacuum is released with nitrogen to atmospheric pressure, and the resulting slurry is heated to 55-60° C. The slurry is then cooled to ambient temperature (15-25° C.) and held for 1 hour. Anhydrous Form S1 of Compound (1) is collected by filtration, and the vessel and filter cake are rinsed with n-heptane (1600 mL). The solid is dried under vacuum maintaining the temperature below 40° C.

Method 2.

Crude Compound (1) (431 g) is dissolved in either dichloromethane (1600 mL) or tetrahydrofuran (2000 mL) with stirring under nitrogen. The solution is transferred through a polish filter (1 μm pore size or smaller) into a second vessel. The solution is concentrated to approximately 1000-1200 mL under partial vacuum while keeping the temperature of the contents ≤40° C. The resulting solution is diluted with 2000 mL isopropyl alcohol and heated to reflux (45-55° C. if using dichloromethane or 70-75° C. if using tetrahydrofuran). The lower boiling solvent is exchanged by adding isopropyl alcohol (5000 mL) slowly while distilling to maintain the contents in the vessel at approximately 3000 mL. At the end of the distillation, the contents are maintained at reflux for at least 15 minutes to ensure any solid has dissolved. The clear solution is cooled to 68-72° C., and Form S1 of Compound (1) seed crystals (4 g, 1% w/w) are added to induce crystallization. After holding for 1 hour to ensure crystallization has started, the contents are cooled to 58-62° C. and held for up to 2 hours. The contents are then slowly cooled to 20-25° C. over approximately 2-3 hours, held for 1 hour, and then cooled further to 0-10° C. After holding for at least 15 minutes, anhydrous Form S1 of Compound (1) is collected by filtration, and the vessel and filter cake are washed with cold isopropyl alcohol (900 mL). The solid is dried under vacuum maintaining the temperature below 40° C.

Form S1 of Compound (1) was characterized using XRPD, TGA/DSC, $^{13}$C solid state NMR, and DVR analyses.

1. XRPD Analysis.

FIG. 1 depicts anon-normalized X-ray powder diffraction pattern for Form S1 of Compound (1). Certain observed XRPD peaks from the non-normalized X-ray powder diffraction pattern and other XRPD data are summarized in Table 2 below.

TABLE 2

XRPD characterization of Form S1 of Compound (1).

| XRPD Peaks | Angle (2-Theta ± 0.2) [°] | d-spacing [Å] | Height [cts] | Relative Intensity [%] |
|---|---|---|---|---|
| 1 | 9.2 | 9.61 | 130.30 | 1.82 |
| 2 | 9.4 | 9.45 | 734.98 | 10.26 |
| 3 | 11.9 | 7.45 | 873.59 | 12.19 |
| 4 | 13.5 | 6.55 | 477.66 | 6.67 |
| 5 | 13.7 | 6.45 | 117.77 | 1.64 |
| 6 | 14.7 | 6.02 | 277.38 | 3.87 |
| 7 | 15.4 | 5.75 | 1267.97 | 17.70 |
| 8 | 15.6 | 5.67 | 7164.28 | 100.00 |
| 9 | 16.3 | 5.45 | 396.41 | 5.53 |
| 10 | 17.3 | 5.13 | 61.38 | 0.86 |
| 11 | 18.1 | 4.91 | 1556.56 | 21.73 |
| 12 | 18.6 | 4.76 | 378.49 | 5.28 |
| 13 | 18.8 | 4.72 | 1946.22 | 27.17 |
| 14 | 19.7 | 4.51 | 541.51 | 7.56 |
| 15 | 20.0 | 4.44 | 135.32 | 1.89 |
| 16 | 20.9 | 4.26 | 117.91 | 1.65 |
| 17 | 22.0 | 4.04 | 490.09 | 6.84 |
| 18 | 22.2 | 4.01 | 757.60 | 10.57 |
| 19 | 22.6 | 3.93 | 3355.82 | 46.84 |
| 20 | 23.4 | 3.81 | 912.74 | 12.74 |
| 21 | 23.9 | 3.72 | 78.49 | 1.10 |
| 22 | 25.1 | 3.55 | 194.23 | 2.71 |
| 23 | 25.7 | 3.46 | 140.53 | 1.96 |
| 24 | 26.0 | 3.43 | 109.47 | 1.53 |
| 25 | 26.3 | 3.38 | 77.29 | 1.08 |
| 26 | 26.9 | 3.32 | 175.48 | 2.45 |
| 27 | 27.9 | 3.20 | 147.57 | 2.06 |
| 28 | 28.1 | 3.17 | 308.90 | 4.31 |
| 29 | 28.8 | 3.10 | 76.19 | 1.06 |
| 30 | 30.2 | 2.96 | 153.13 | 2.14 |
| 31 | 30.5 | 2.93 | 110.65 | 1.54 |
| 32 | 31.1 | 2.87 | 375.75 | 5.24 |
| 33 | 32.9 | 2.72 | 52.07 | 0.73 |

2. TGA/DSC Analysis.

Figure 2:
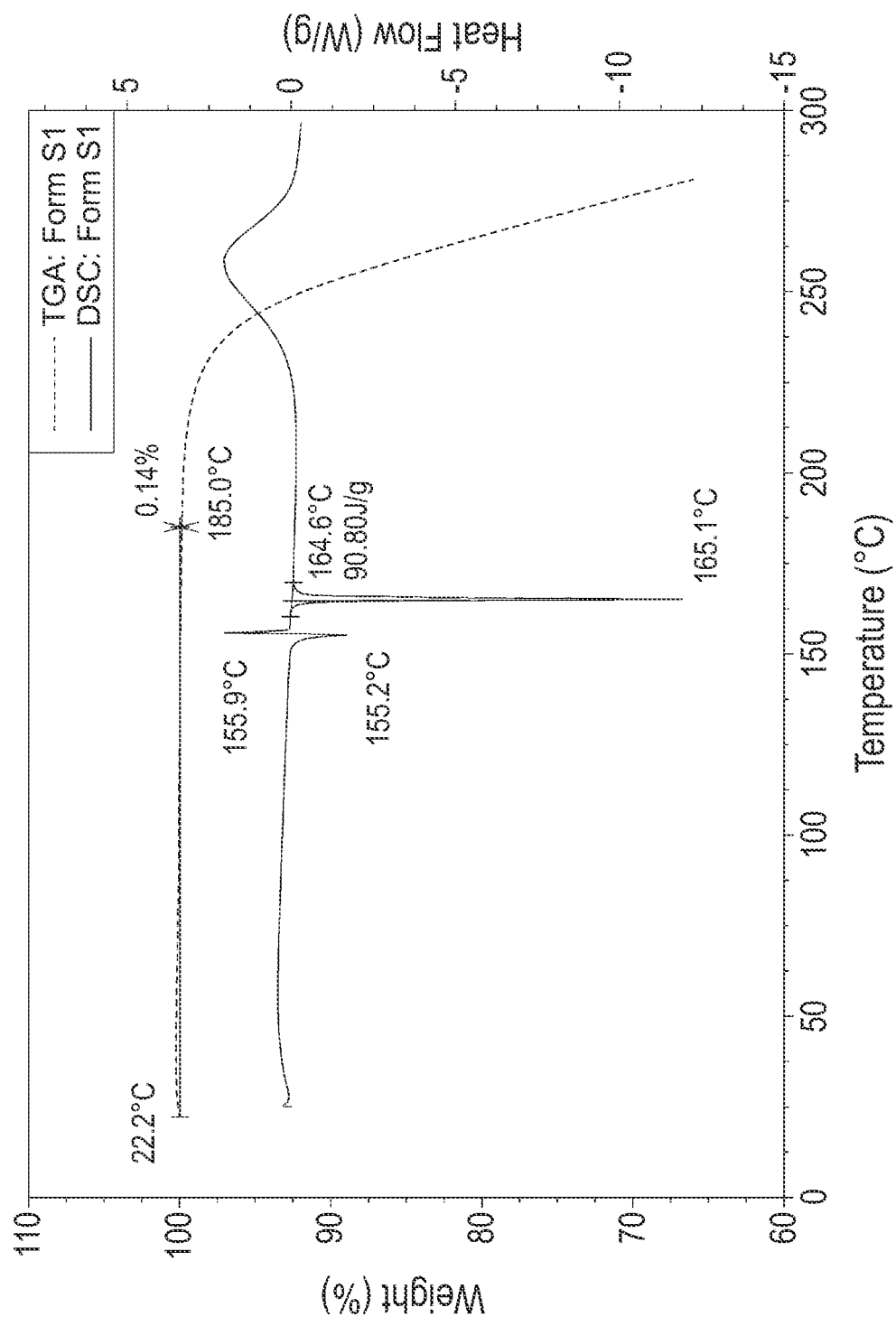
FIG. 2 depicts an exemplary thermogram of a TGA/DSC thermal analysis of Form S1 of Compound (1) including a TG curve and DSC curve.

Referring to FIG. 2, the TGA analysis of Form S1 of Compound (1) presented a weight loss of 0.100 up to 185° C. on the TGA curve. The DSC analysis of Form S1 of Compound (1) presented melting-crystallization-melting transitions at 155° C., 155.9° C., and 165.1° C. The results of these thermal analyses demonstrate that Form S1 of Compound (1) converts to Form S4 under heating conditions.

3. $^{13}$C Solid State NMR Analysis.

Figure 3:
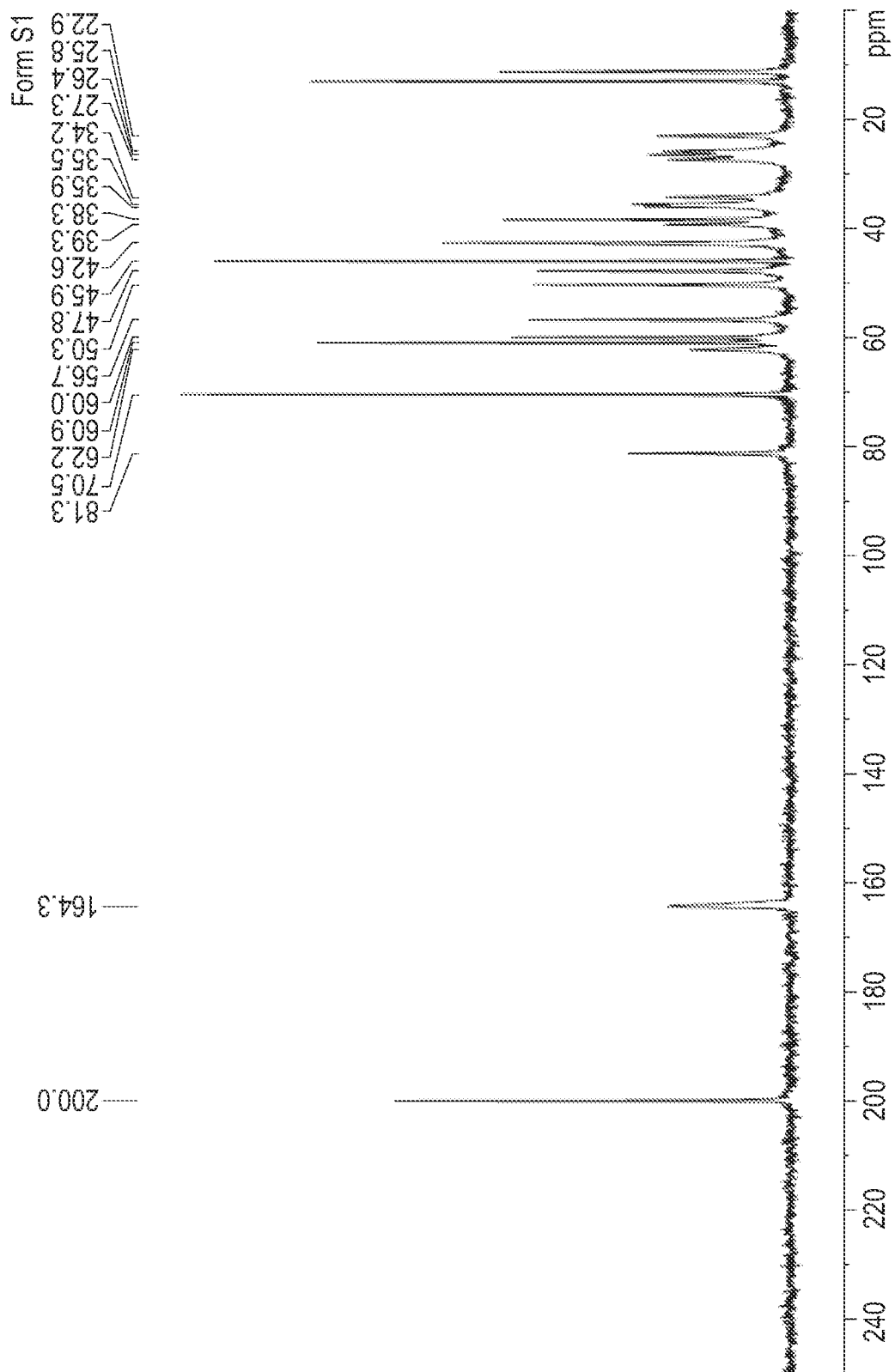
FIG. 3 depicts an exemplary $^{13}C$ solid state NMR spectrum of Form S1 of Compound (1).

FIG. 3 depicts the $^{13}$C solid state NMR spectrum for Form S1 of Compound (1). Certain observed peaks from the NMR spectrum are summarized in Table 3 below. A single pure phase was observed during the $^{13}$C solid state NMR analysis of Form S1 of Compound (1).

TABLE 3

$^{13}$C SSNMR characterization of Form S1 of Compound (1). Peaks (ppm)

| |
|---|
| 200 |
| 164.3 |
| 81.3 |
| 70.5 |
| 62.2 |
| 60.9 |
| 60.0 |
| 56.7 |
| 50.3 |
| 47.8 |
| 45.9 |
| 42.6 |
| 42.8 |
| 39.3 |
| 38.3 |
| 35.9 |
| 35.5 |
| 34.2 |
| 27.3 |
| 26.4 |
| 25.8 |
| 22.9 |
| 13.2 |
| 11.4 |

4. DVS Analysis.

Figure 4:
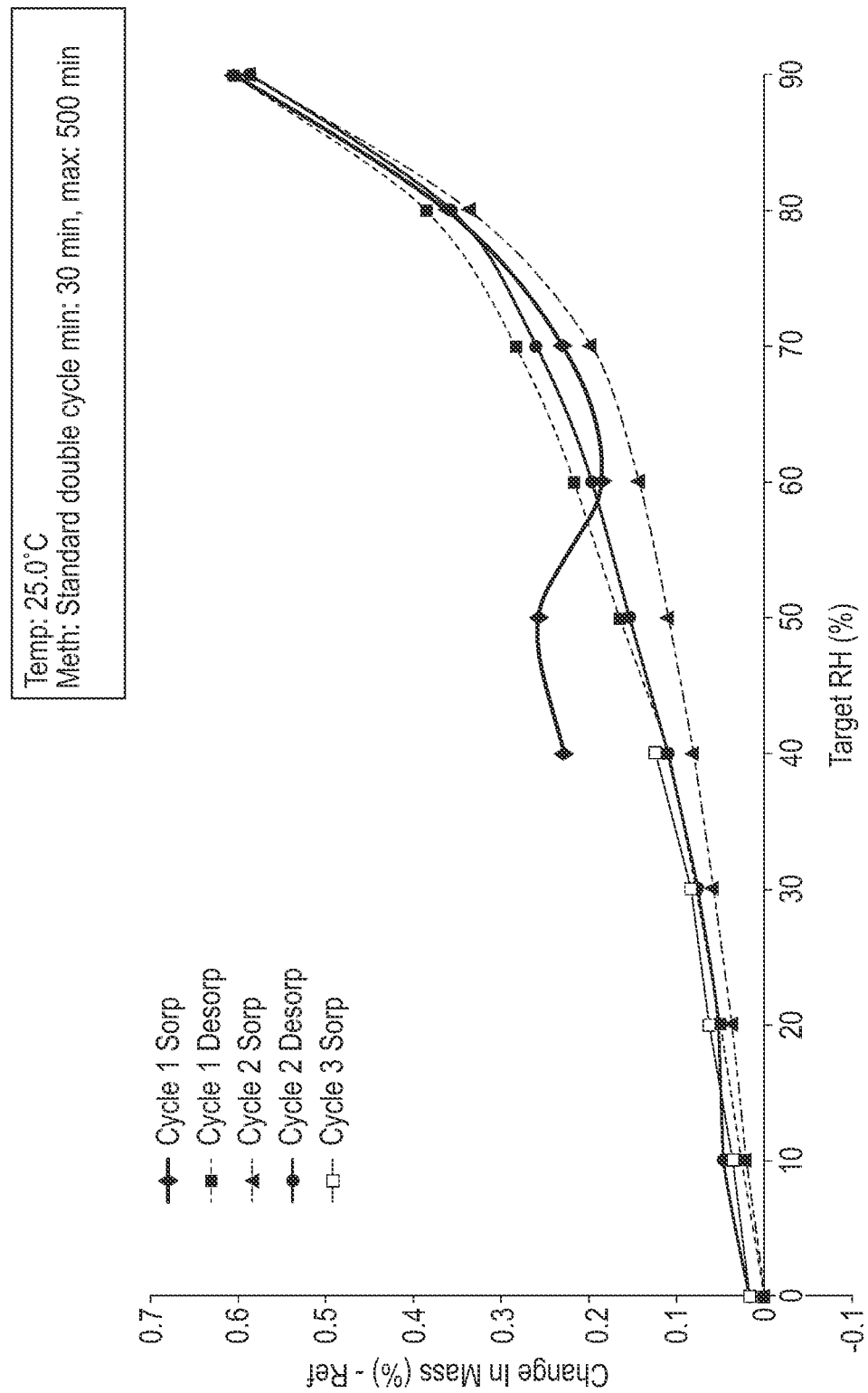
FIG. 4 depicts an exemplary DVS isotherm plot of Form S1 of Compound (1) at 25° C.

Referring to FIG. 4, the DVS analysis of Form S1 of Compound (1) indicated that Form S1 is substantially non-hygroscopic by DVS with a mass uptake of ca. 0.6 wt. % (0.14 eq. water) at 90% RH. No change was observed to the XRPD pattern of the sample following the DVS analysis, which indicated that if the sample underwent a form change during the DVS analysis, the sample returned to Form S1 prior to XRPD analysis.

Example No. 2: Preparation of Form S4 of Compound (1)

Crude Compound (1) (431 g) is dissolved in tetrahydrofuran (2000 mL) with stirring under nitrogen. N-Heptane (400 mL) is added, and then the solution is heated to reflux at atmospheric pressure (70-75° C.), and the solvent is exchanged by adding n-heptane (5000 mL) slowly while distilling to maintain the volume in the vessel at approximately 2500 mL. Compound (1) begins to crystallize when the temperature reaches 85-90° C. At the end of the distillation, the resulting slurry is cooled to ambient temperature (15-25° C.) and held for 1 hour. Anhydrous Form S4 of Compound (1) is collected by filtration, and the vessel and filter cake are rinsed with n-heptane (900 mL). The solid is dried under vacuum maintaining the temperature below 40° C.

Form S4 of Compound (1) was characterized using XRPD, TGA/DSC, $^{13}$C solid state NMR, and DVR analyses.

1. XRPD Analysis.

FIG. 5 depicts a non-normalized X-ray powder diffraction pattern for Form S4 of Compound (1). Certain observed XRPD peaks from the non-normalized X-ray powder diffraction pattern and other XRPD data are summarized in Table 4 below.

TABLE 4

XRPD characterization of Form S4 of Compound (1).

| XRPD Peaks | Angle (2-Theta ± 0.2) [°] | d-spacing [Å] | Height [cts] | Relative Intensity [%] |
|---|---|---|---|---|
| 1 | 8.9 | 9.89316 | 466.84 | 27.36 |
| 2 | 9.6 | 9.25209 | 72.63 | 4.26 |
| 3 | 11.6 | 7.60842 | 175.27 | 10.27 |
| 4 | 12.9 | 6.84691 | 81.97 | 4.80 |
| 5 | 14.6 | 6.06120 | 1706.51 | 100.00 |
| 6 | 15.0 | 5.90644 | 362.07 | 21.22 |
| 7 | 16.4 | 5.40247 | 1106.64 | 64.85 |
| 8 | 17.4 | 5.08518 | 368.31 | 21.58 |
| 9 | 18.0 | 4.93806 | 860.17 | 50.41 |
| 10 | 20.0 | 4.43231 | 1496.11 | 87.67 |
| 11 | 21.2 | 4.19568 | 124.92 | 7.32 |
| 12 | 22.5 | 3.95642 | 54.85 | 3.21 |
| 13 | 23.3 | 3.81774 | 38.36 | 2.25 |
| 14 | 25.1 | 3.55221 | 65.66 | 3.85 |
| 15 | 26.2 | 3.40780 | 85.51 | 5.01 |
| 16 | 29.0 | 3.07881 | 102.24 | 5.99 |
| 17 | 29.6 | 3.02273 | 94.84 | 5.56 |
| 18 | 30.9 | 2.89665 | 56.05 | 3.28 |

Figure 6:
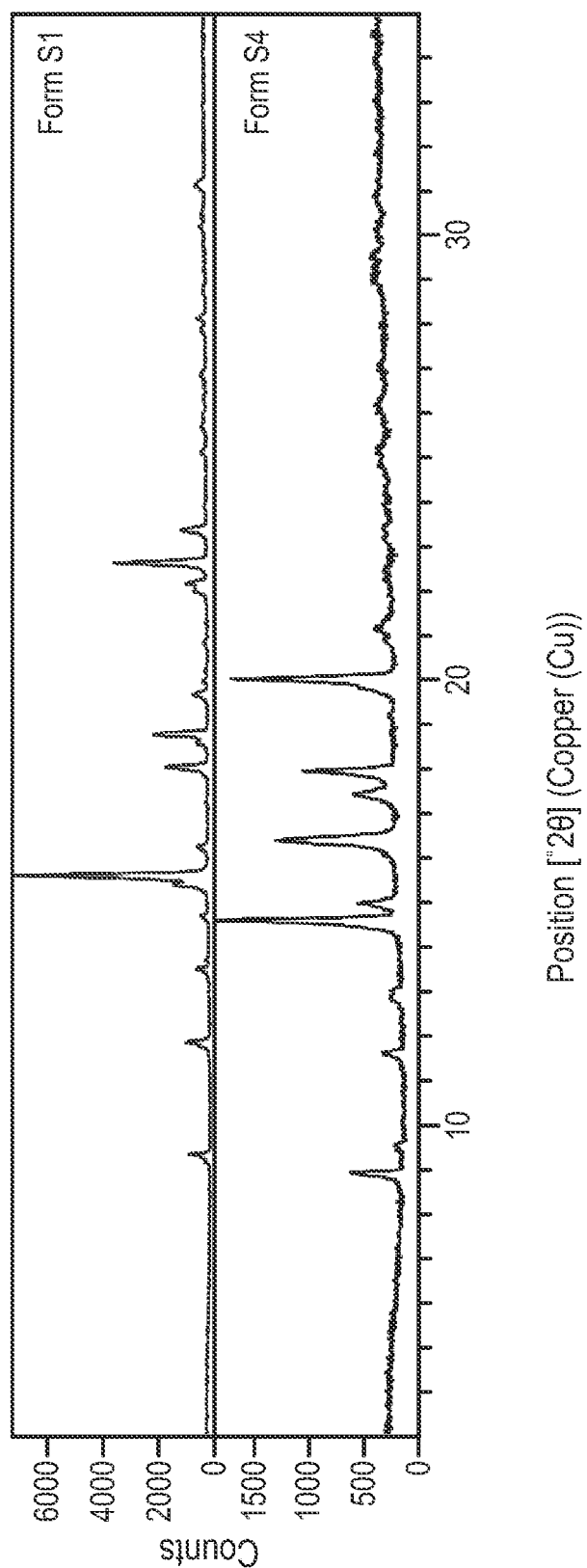
FIG. 6 depicts exemplary XRPD patterns for Form S1 (top) and Form S4 (bottom) of Compound (1).

FIG. 6 provides stacked non-normalized X-ray diffraction patterns for Forms S1 (top) and S4 (bottom) of Compound (1).

2. TGA/DSC Analysis

Figure 7:
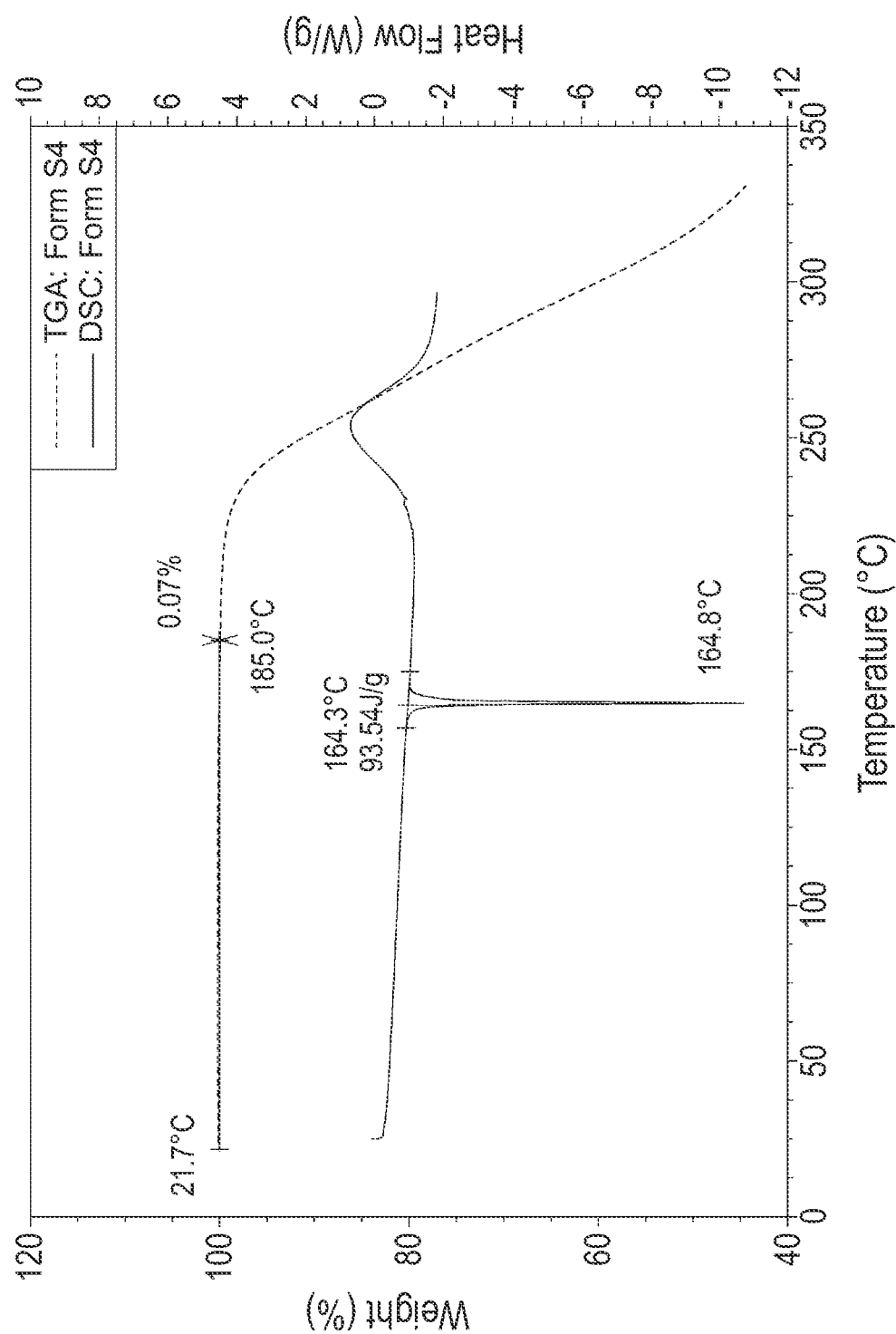
FIG. 7 depicts an exemplary thermogram of a TGA/DSC thermal analysis of Form S4 of Compound (1) including a TG curve and DSC curve.

Referring to FIG. 7, the TGA analysis of Form S4 of Compound (1) presented a weight loss of 0.100 up to 185° C. on the TGA curve. The DSC analysis of Form S4 of Compound (1) presented melting endotherm at 164.8° C. before decomposition.

Figure 8:
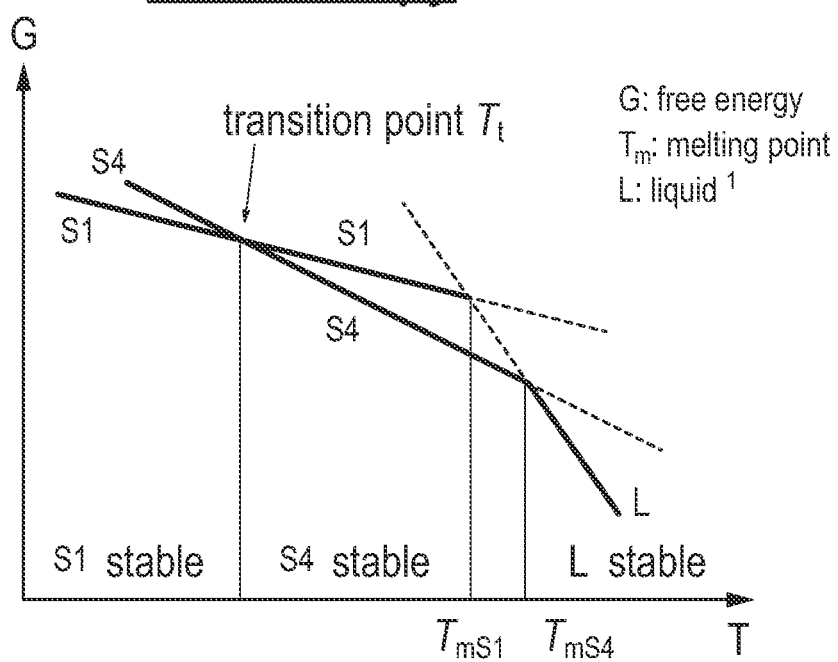
FIG. 8 is an enantiotropy diagram illustrating the relationship between Form S1 and Form S4 of Compound (1).

The DSC data generated in the DSC analysis of Form S1 and Form S4 demonstrates an enantiotropic relationship between Form S1 and Form S4 as illustrated in FIG. 8.

3. $^{13}$C Solid State NMR Analysis.

Figure 9:
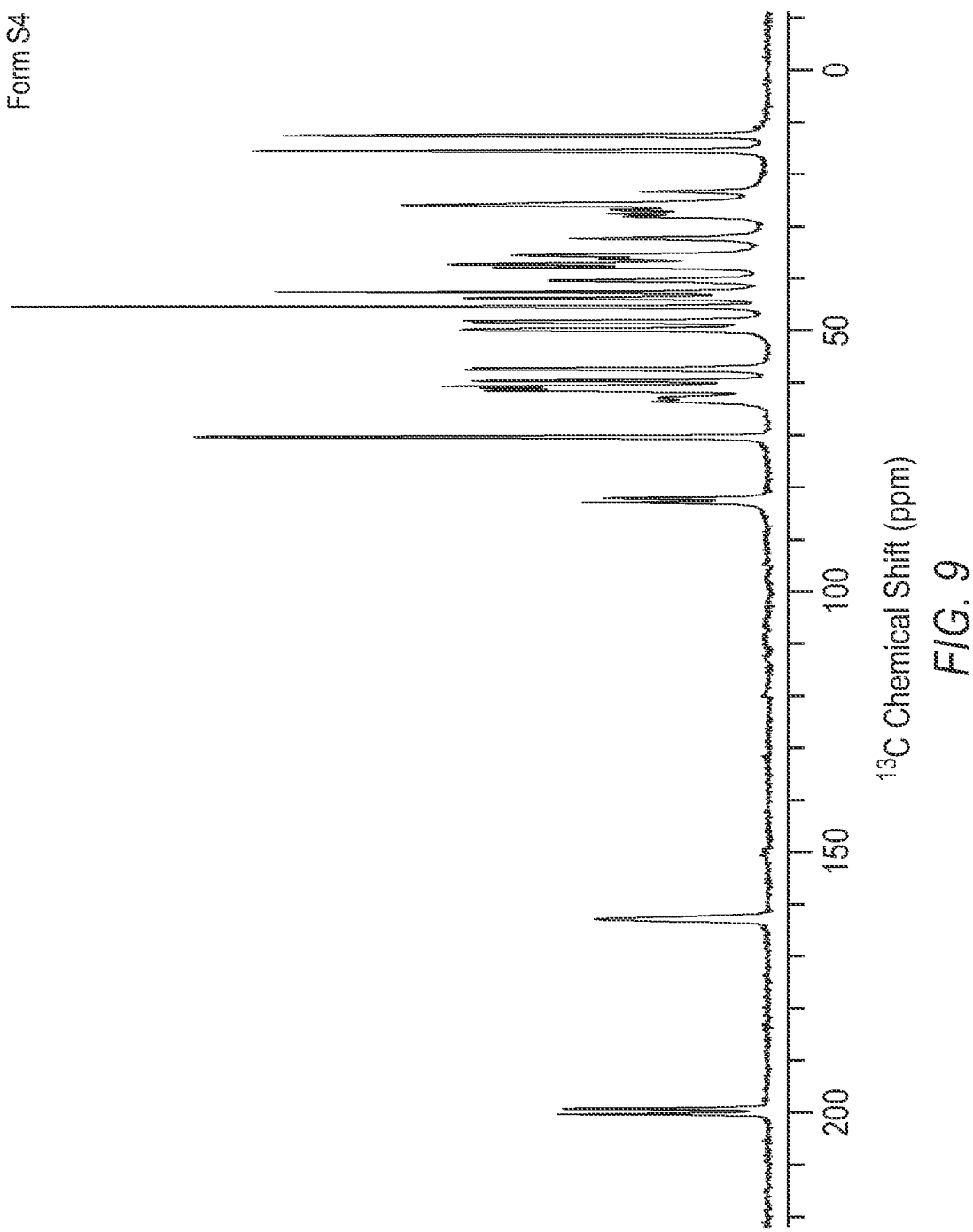
FIG. 9 depicts an exemplary $^{13}C$ solid state NMR spectrum of Form S4 of Compound (1).

FIG. 9 depicts a $^{13}$C solid state NMR spectrum for Form S4 of Compound (1). Certain observed peaks from the NMR spectrum are summarized in Table 5 below. A single pure phase was observed during the $^{13}$C solid state NMR analysis of Form S4 of Compound (I).

TABLE 5

$^{13}$C SSNMR characterization of Form S1 of Compound (1). Peaks (ppm)

| |
|---|
| 200.2 |
| 199.1 |
| 162.8 |
| 82.9 |
| 82.1 |
| 70.4 |
| 63.6 |
| 62.9 |
| 61.4 |
| 61 |
| 60.8 |
| 59.6 |

TABLE 5-continued

13C SSNMR characterization of Form S1 of Compound (1). Peaks (ppm)

57.5
57.2
49.9
49.7
48.4
48.1
45.4
43.8
42.6
40.3
37.9
37.3
36.2
35.5
32.3
28.1
27.5
26.8
25.9
23.3
15.5
12.6

Figure 10:
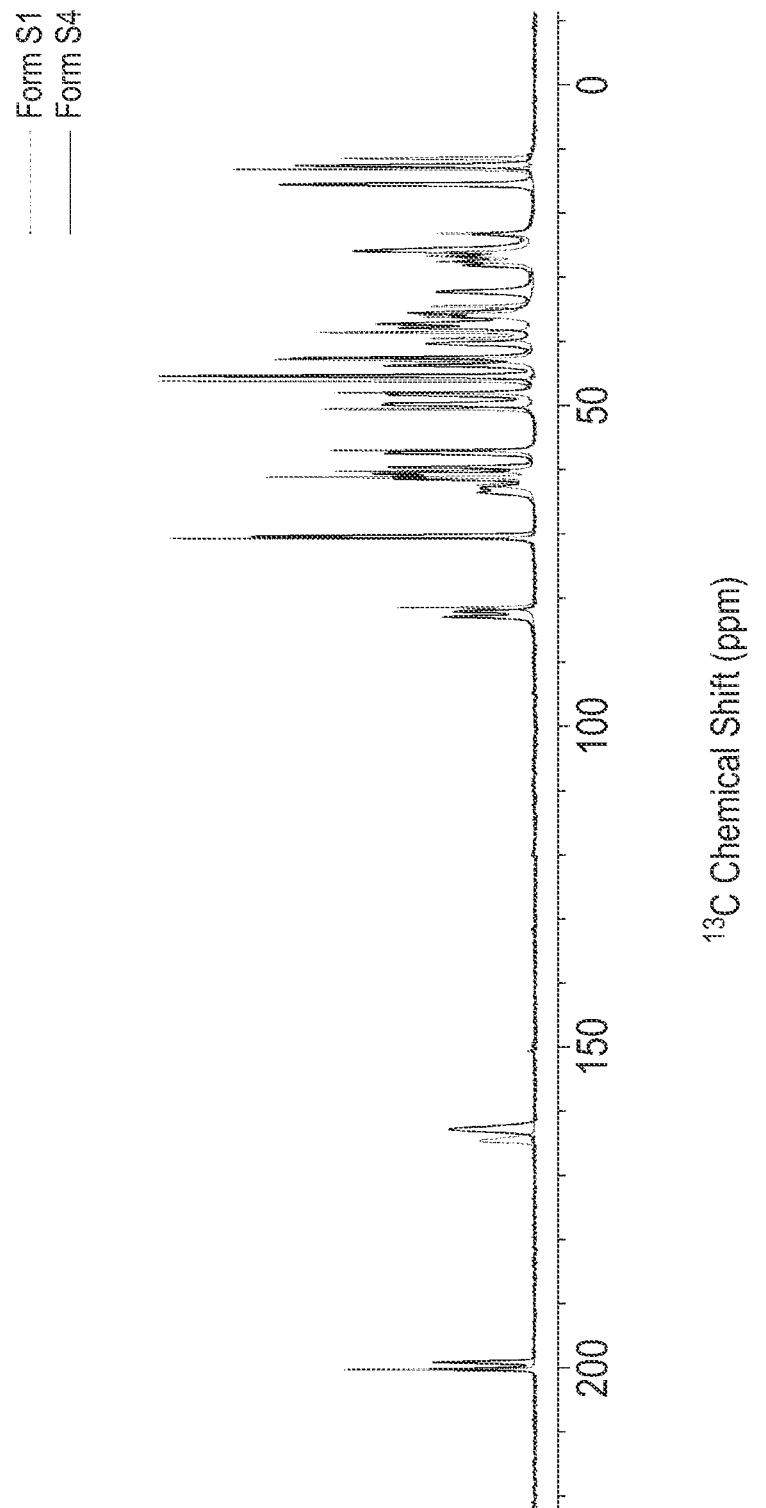
FIG. 10 depicts an overlay of exemplary $^{13}C$ solid state NMR spectra for Form S1 (solid lines) and Form S4 (dashed lines) of Compound (1).

FIG. 10 presents an overlay of the 13C SSNMR spectra for Form S1 of Compound (1) and Form S4 of Compound (1) for comparison.

4. DVS Analysis

Figure 11:
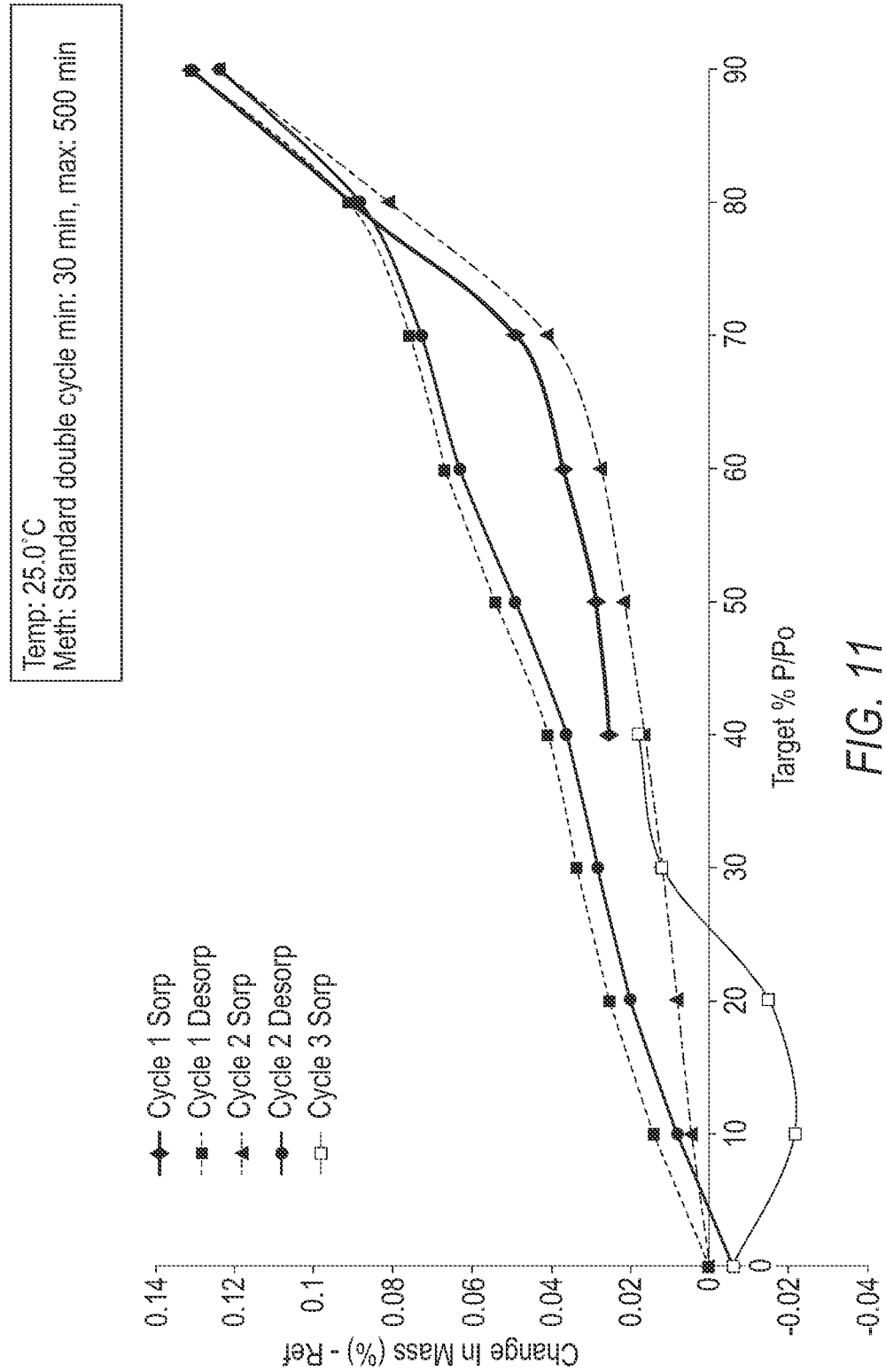
FIG. 11 depicts an exemplary DVS isotherm plot of Form S4 of Compound (1) at 25° C.

Referring to FIG. 11, a DVS analysis of Form S4 of Compound (1) indicates that Form S4 is non-hygroscopic by DVS with a mass uptake of ca. 0.12 wt. % (0.02 eq. water) at 90% RH. No change was observed to the XRPD pattern of the sample following the DVS analysis, which indicated that if sample underwent a form change during the DVS analysis, the sample returned to Form S4 prior to XRPD analysis.

Example 3: Slurry Conversion of Form S1 and Form S4 of Compound (1)

To verify the transition temperature between Form S1 and Form S4 of Compound (1) calculated from the DSC data, competitive slurry experiments of Form S1 and Form S4 were performed.

In each experiment, slurries were generated using approximately equal amounts of Form S1 and Form S4. The forms were suspended in 0.3 mL of solvent in a 1.5 mL glass vial. The suspensions were stirred (1000 rpm) magnetically for four (4) days at the target temperatures. The remaining solids were isolated via centrifugation (10000 rpm, 3 min) and analyzed using the XPRD analysis method described above. The experimental conditions and results are summarized in Table 10.

TABLE 10

Summary of competitive slurry experiments of Form S1 and Form S4.

| Experiment | Form S1 (mg) | Form S4 (mg) | Solvent | Temp. (° C.) | Time Point (hr) | Results |
|---|---|---|---|---|---|---|
| 5A | 10.2 | 10.1 | IPA | 60 | 1 | Form S1 |
| 5B | 9.9 | 10.1 | IPA | 70 | 1 | Form S1 |
| 5C | 10.3 | 10.2 | IPA | 80 | — | Form S4 |

Figure 12:
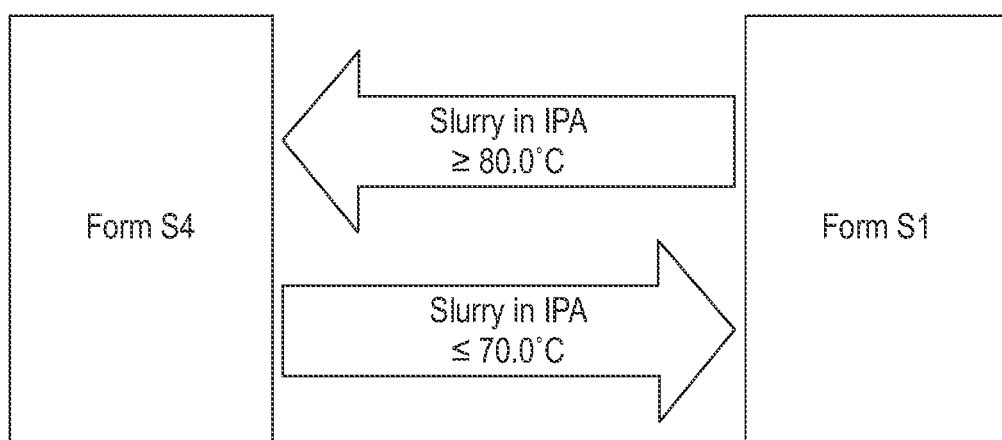
FIG. 12 is a diagram illustrating interconversion conditions for Form S1 and Form S4 of Compound (1).

As illustrated in FIG. 12, the results of this experiment demonstrated that Form S4 converted to Form S1 at 60° C. and 70° C., while Form S1 converted to Form S4 at 80° C.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

OTHER EMBODIMENTS

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A crystalline form of Compound (1), wherein Compound (1) is represented by the following structural formula:

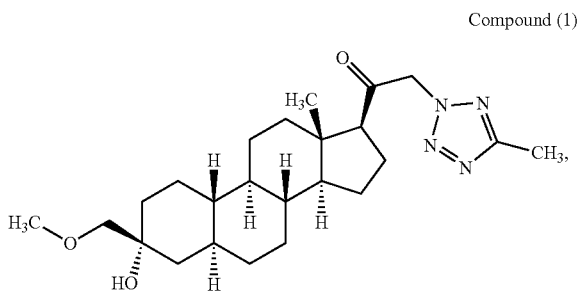

Compound (1)

wherein the crystalline form is crystalline anhydrous Compound (1), and wherein the crystalline form is characterized by one or more peaks corresponding to 2-theta values measured in degrees of 15.4±0.3, 15.6±0.3, 18.1±0.3, 18.8±0.3, and 22.6±0.3 in an X-ray powder diffraction pattern.

2. The crystalline form of claim 1, wherein the crystalline form is further characterized by one or more peaks corresponding to 2-theta values measured in degrees of 9.4±0.3, 11.9±0.3, 22.2±0.3, and 23.4±0.3 in an X-ray powder diffraction pattern.

3. The crystalline form of claim 1, wherein the crystalline form has an endotherm at a $T_{onset}$ from about 146° C. to about 157° C. when heated at a rate of 10 ° C./min starting at a temperature of about 30° C.

4. The crystalline form of claim 1, wherein the crystalline form is characterized by one or more peaks corresponding to 200.0±0.3 ppm, 164.3±0.3 ppm, 81.3±0.3 ppm, 70.5±0.3 ppm, and 62.2±0.3 ppm in a $^{13}$C SSNMR spectrum.

5. The crystalline form of claim 4, wherein the crystalline form is further characterized by one or more peaks corresponding to 60.9±0.3 ppm, 60.0±0.3 ppm, 56.7±0.3 ppm, 47.8±0.3 ppm, and 45.9±0.3 ppm in a $^{13}$C SSNMR spectrum.

6. The crystalline form of claim 5, wherein the crystalline form is further characterized by one or more peaks corresponding to 42.6±0.3 ppm, 39.3±0.3 ppm, 38.3±0.3 ppm, 35.5±0.3 ppm, 25.8±0.3 ppm, and 22.9±0.3 ppm in a $^{13}$C SSNMR spectrum.

7. A pharmaceutical composition comprising a crystalline form of claim 1, and a pharmaceutically acceptable excipient.

* * * * *